(12) United States Patent
Dawkins et al.

(10) Patent No.: US 6,383,747 B1
(45) Date of Patent: May 7, 2002

(54) METHOD FOR DETERMINING ANCESTRAL HAPLOTYPES USING HAPLOSPECIFIC GEOMETRIC ELEMENTS WITHIN THE MAJOR HISTOCOMPATIBILITY COMPLEX MULTIGENE CLUSTER

(75) Inventors: Roger Letts Dawkins, Canningvale; Lawrence Joseph Abraham, Cottesloe, both of (AU)

(73) Assignee: The Immunogenetics Research Foundation Incorporated, Western Australia (AU)

( * ) Notice: Subject to any disclaimer, the term of this patent is extended or adjusted under 35 U.S.C. 154(b) by 0 days.

(21) Appl. No.: 09/281,481

(22) Filed: Mar. 30, 1999

Related U.S. Application Data

(63) Continuation of application No. 08/893,971, filed on Jul. 16, 1997, now abandoned, which is a continuation of application No. 08/232,229, filed as application No. PCT/AU92/00583 on Oct. 30, 1992, now abandoned.

(30) Foreign Application Priority Data

Nov. 1, 1991  (AU) ......................................... PK 9279/91

(51) Int. Cl.[7] ................................................. C12Q 1/68
(52) U.S. Cl. ........................................... 435/6; 435/91.2
(58) Field of Search ..................................... 435/6, 91.2

(56) References Cited

FOREIGN PATENT DOCUMENTS

| AU | B25138/84 | 9/1985 |
| WO | WO 92/01066 | 1/1992 |
| WO | WO 89/11547 | 11/1998 |

OTHER PUBLICATIONS

Tays et al. Bone Marrow Transplantation 15:381–385, 1995.*
Marshall et al. Genomics 17:435–441, 1993.*
Degli–Esposti et al. Human Immunogenetics 34:242–252, 1992.*
Wu et al. Human Immunology 33:89–97, 1992.*
Degli–Esposti et al. Immunogenetics 36:345–356, 1992.*
Leelayuwat et al. Immunogenetics 36:208–212, 1992.*
Abraham et al. Tissue Antigens 39:117–121, 1992.*
Luo et al. Mol. Biol. 187:325–340, 1986.*
Karathanasis et al. Nature 30:371–373, 1983.*
Hourcade et al. Genomics 12(2): 289–300, 1992.*
Dawkins et al. (1989) "Some Disease–Associated Ancestral Haplotypes Carry a Polymorphism of TNF", *Human Immunology* 26: 91–97.
Lo et al. (1991) "Direct Haplotype Determination by Double ARMS: Specificity, Sensitivity and Genetic Applications", *Nucleic Acids Research* 19 (13): 3561–3567.
Tokunaga et al. (1989) "Comparative Mapping of the Human Major Histocompatibility Complex in Different Racial Groups by Pulsed Field Gel Electrophoresis", *Human Immunology* 26:99–106.
Tokunaga et al. (1991) "The Genomic Structure of two Ancestral Haplotypes Carrying C4A Duplications", *Immunogenetics* 34: 247–251.

* cited by examiner

Primary Examiner—Lisa B. Arthur
(74) *Attorney, Agent, or Firm*—Scully, Scott, Murphy & Presser

(57) ABSTRACT

The present invention relates to haplotype-specific genomic elements (HGEs) present in multigene complexes of higher organisms. The present invention provides the genetic characterizations of the HGEs for the human Major Histocompatibility Complex. The present invention further relates to a method of determining the ancestral haplotypes of higher organisms by using approaches based on HGEs. The method of the present invention can be applied to distinguish haplotypic differences in genes of multigene complex, such as MHC genes, which is very useful in clinical applications.

5 Claims, 35 Drawing Sheets

| | Modified 57.1 | CLI Sequence | | | | | | | | |
|---|---|---|---|---|---|---|---|---|---|---|
| | 10 | 20 | 30 | 40 | 50 | 60 | 70 | 80 | 90 | 100 |
| 57.1 6.5 | CCTTCATATT | TTCATGTCAT | TGAATCTTTC | TTAAAGTGCC | TTTGAAAGAG | ATGTTTTCAG | TGGAATAGAG | AGATGTGTAA | CAATATTTAC | AAAAGGCGTT |
| | 110 | 120 | 130 | 140 | 150 | 160 | 170 | 180 | 190 | 200 |
| 57.1 6.5 | GGCTGTAATA | AAAAGGGAAA | CGCAAATGAG | TGGGGACACA | GGGGACCCTG | TTCCATTTAT | TCTCAAAGCA | CGTTTGAAAA | CTCCCTTGCC | ATACCGTCCT |
| | 210 | 220 | 230 | 240 | 250 | 260 | 270 | 280 | 290 | 300 |
| 57.1 6.5 | TGGATGGAGA | CAAAGTCGAG | GCAGATCTTG | TTCCTGGAGT | ATTGCATTTGA | TTTTGGAAAC | GGTCCAAGGC | TTTCAGGAAT | CAGGCTGACT | TAGATCTAAA |
| | 310 | 320 | 330 | 340 | 350 | 360 | 370 | 380 | 390 | 400 |
| 57.1 6.5 | GTCTCAAGAA | TGTTCGTTCT | AGCAGTGAGC | CTGTGAGAAG | AATCTAGCCC | ATCTGGGCCA | TGCTCTCTCT | GCTTTCACCT | AGTGGCAGTG | GTTGGAAGGA |
| | 410 | 420 | 430 | 440 | 450 | 460 | 470 | 480 | 490 | 500 |
| 57.1 6.5 | CAGGGCACAG | TGTTACTGCA | TGGGTGGGGC | TGAAGCCAAG | GTCAAAACCGC | CTTTGCGSAAA | TTATAAGTAA | GGAAATGATG | ACAGTGAAAG | ACATCAAACC |
| | 510 | 520 | 530 | 540 | 550 | 560 | 570 | 580 | 590 | 600 |
| 57.1 6.5 | TAACTCACCC | TATCTTGCTT | CTAACCGCTA | ACCTGCCCTT | GTTCATTTCT | GGGCATAGCC | CGAACTAGCC | TGGGAAGGA | ATTTATAGTT | TAAAGCGAAA |
| | 610 | 620 | 630 | 640 | 650 | 660 | 670 | 680 | 690 | 700 |
| 57.1 6.5 | GTGTTCTTTT | AAAACGAATG | AAAAGCCCGCC | AGCCATTAAG | TTAGGATGAG | AGGGGCTGGA | AGGGGCTCGA | ATTCTGAATA | TTACCAGCCA | TTATTCCGGA | GGTCATAAGA |
| | 710 | 720 | 730 | 740 | 750 | 760 | 770 | 780 | 790 | 800 |
| 57.1 6.5 | TTTGCAACTT | CCCCAGTTAC | TCTTGAAGGT | AACATCACTA | TGTGAACCT | CAGAGCGGCC | TTTGAGATG | TATTTTCAT | TTCTTTTTTC | TTTTCTTTC |
| | 810 | 820 | 830 | 840 | 850 | 860 | 870 | 880 | 890 | 900 |
| 57.1 6.5 | TTTCTTTTCT | TTTCTTTTTT | TTTTTTTTT | TTTTGACGGA | GTCTCGCTCT | GTCGCCCAGG | CTGGAGTGCA | GTGGCGCGAT | CTCGGCTCAC | TGCAAGCTCC |
| | 910 | 920 | 930 | 940 | 950 | 960 | 970 | 980 | 990 | 1000 |
| 57.1 6.5 | GCCTCCCGGG | TTCACGTCAT | TCTCCTTCCT | CAGCCTACTC | AGTAGCTGGG | CCCGCCACCA | CCCGCCACCA | CACCCGGCTA | ATTTTTTTGTA | TTTTTAGTAG |

| | | 1010 | 1020 | 1030 | 1040 | 1050 | 1060 | 1070 | 1080 | 1090 | 1100 |
|---|---|---|---|---|---|---|---|---|---|---|---|
| 57.1 | 6.5 | AGACGGGGTT | TCACCGTGTT | AGCAAGGATG | GTCTCCATCT | CCTGACCTCG | TGATCGGCCC | GCCTCGGGCT | CCCAAGTGC | TGGATTACA | GGGCTGAGCA |
| | | 1110 | 1120 | 1130 | 1140 | 1150 | 1160 | 1170 | 1180 | 1190 | 1200 |
| 57.1 | 6.5 | CCACGCCAGG | CCAGTTTTTT | GCATTTCTAA | CAACTGGAGG | ACCCCATCTG | GACCTGCCAA | CCAGTCCTCT | GGCCCCCCAC | TCAGGAACTG | ACTCAGCCTA |
| | | 1210 | 1220 | 1230 | 1240 | 1250 | 1260 | 1270 | 1280 | 1290 | 1300 |
| 57.1 | 6.5 | AGAGAACAGC | TCCACTCACT | ATGATTTCAT | ACCGGGGCCA | ACCAATCAGC | ACTCCTGATT | CACTGGGCCC | CCCTATCCAC | CAAATTATCC | TTAAAAACTG |
| | | 1310 | 1320 | 1330 | 1340 | 1350 | 1360 | 1370 | 1380 | 1390 | 1400 |
| 57.1 | 6.5 | ATCAGAGTTT | TCGGGGAGAC | AGATTTGAGT | AATAAAACTC | TGGTCTCCCG | CACGGCCGGC | TCTGCATGAA | TTACTCTTTC | TCTATTGTAA | TTCCCCTGCC |
| | | 1410 | 1420 | 1430 | 1440 | 1450 | 1460 | 1470 | 1480 | 1490 | 1500 |
| 57.1 | 6.5 | TTGATAAATC | GGCTTTGTCT | AGGCAGTCAG | CAAGGTGAAC | ACACTGGGTG | GTTACAAAGG | GAGTCCAGGC | CACTGTGCAG | GATGTGCTTT | GCTGTAGTGG |
| | | 1510 | 1520 | 1530 | 1540 | 1550 | 1560 | 1570 | 1580 | 1590 | 1600 |
| 57.1 | 6.5 | GGTCCGGGTA | GCGGAGGAAA | GTCAAGGACA | CTCAGGGAAT | AAATGGCAGA | GGAAGAAGGA | GCACGAGGGA | GGACCCAAAG | CCTCCAGACC | TCTCCTTCCT |
| | | 1610 | 1620 | 1630 | 1640 | 1650 | 1660 | 1670 | 1680 | 1690 | 1700 |
| 57.1 | 6.5 | TCTCTCCCTG | TTAGGGTTGG | AGAGGACCAG | CGTGGTCCCA | GGAGGGATGG | CTGGTGGGGT | GCAGAAAACG | CCCTGGTTGC | AAAGGGGGGT | CACGCGCCCC |
| | | 1710 | 1720 | 1730 | 1740 | 1750 | 1760 | 1770 | 1780 | 1790 | 1800 |
| 57.1 | 6.5 | ACACAAGGGT | CCTGGCCTGT | AGCTGCTACT | CATGAGTTCA | AATTAGGAGG | AGACTCACAC | GTGTCCTTTG | CAAGGTAGAC | TCCTTATCTC | CCGCTCCGGC |
| | | 1810 | 1820 | 1830 | 1840 | 1850 | 1860 | 1870 | 1880 | 1890 | 1900 |
| 57.1 | 6.5 | TGGGTTCCCA | AATCCATCCT | GATAAAGCAG | AAAAACCAAG | AGCCAAATTC | TGCGTGGGAC | CTTTCTGACA | GCTGGAAGGT | CCTCCCCCTC | CCCATTCCTC |
| | | 1910 | 1920 | 1930 | 1940 | 1950 | 1960 | 1970 | 1980 | 1990 | 2000 |
| 57.1 | 6.5 | ACATGTGCCC | TTCTTGCCCT | GCCCCCCTCCA | CTTTGTCTCC | ACTTCCTCAT | CCTTTTCCCT | CTCCGGACC | CGCTCCTGAG | TATCTCCCGC | CTTCTTCAGA |

Figure 1b

| | | | | | | | | | |
|---|---|---|---|---|---|---|---|---|---|
| 4010 | 4020 | 4030 | 4040 | 4050 | 4060 | 4070 | 4080 | 4090 | 4100 |

57.1 6.5  TTCACACTCG GGACCATCC ACATCCAGG CGTGCAGGGG AGGGGCCCAG GTGAGAGCCC AACCCCTGCC TAGGCTGTGG CTGCACGGGG

| 4110 | 4120 | 4130 | 4140 | 4150 | 4160 | 4170 | 4180 | 4190 | 4200 |

57.1 6.5  GTCCCAGCCC TCCTGGAGCT ATCATTCTTT ATCTCCCTGAA GACCCCGGAC CCCACATAC AAAACTCTG CATTTCTGGT GGACCGGTCT TCTCTTTTGA

| 4210 | 4220 | 4230 | 4240 | 4250 | 4260 | 4270 | 4280 | 4290 | 4300 |

57.1 6.5  GATGTAAACA CTACTTCTCG AATCTTAAAG CCAGCCATTG CCACTCCTAA GGGATAAGCC TCTAACTCCA CTGAAATTAG CCTCAGAATT TCAGCTGAGC

| 4310 | 4320 | 4330 | 4340 | 4350 | 4360 | 4370 | 4380 | 4390 | 4400 |

57.1 6.5  ATTTGGAGCC ACAGGCAGGA AGTCTGTGGG ATTTGTACCT GGCTGATCTG GAAGGTGGTC CTGAAAGTA GTGTGTGACT AGGTGGGCTT TGAGGGGCAT

| 4410 | 4420 | 4430 | 4440 | 4450 | 4460 | 4470 | 4480 | 4490 | 4500 |

57.1 6.5  CGAAGTCCCT GATGAGAGGA GAACAAGACA GATGGGAAGG TTCCGAAAGT GAATTTCAGT CCCAGCACTA CGGATTTGGAA AATCTTTTCC

| 4510 | 4520 | 4530 | 4540 | 4550 | 4560 | 4570 | 4580 | 4590 | 4600 |

57.1 6.5  CAGCCACTTT TGGCCTCTGG GTTTCATTC TGCTTTCCTG TCTGCCAAGC CATTCCAGGC AATCCCTTCA TTTGGTAAAC ATTTATCAA TACCTACTGT

| 4610 | 4620 | 4630 | 4640 | 4650 | 4660 | 4670 | 4680 | 4690 | 4700 |

57.1 6.5  GCCTGGGGCA TTGTTTTAAG AGGAGCTGGA ACTGAGGTAA GAGGAAATAA ACCCTCCTTG CCCTCAAGCC GTGCCCAGTC TTGCTCAGCC AGAGATCAGT

| 4710 | 4720 | 4730 | 4740 | 4750 | 4760 | 4770 | 4780 | 4790 | 4800 |

57.1 6.5  AAGGAAATCA TAAACACAAAT TGAGAGAGAA AAAAAGGAAG AAACTGGTCA GGCGGGCAGT TATGGTGGGT TCTCAGTTGA ATTATTCAA ACAAAGAAC

| 4810 | 4820 | 4830 | 4840 | 4850 | 4860 | 4870 | 4880 | 4890 | 4900 |

57.1 6.5  GTCCTGCAGG CACAGAGAAG GAACTTGCA CAGGGGGGCT TGCCTAAGAC ATGCCCACAG CTGCACAAAT AAGAAAGGCT GCCACAGGAGA CTTGTCCAGA

| 4910 | 4920 | 4930 | 4940 | 4950 | 4960 | 4970 | 4980 | 4990 | 5000 |

57.1 6.5  CATGCCCCGCA ATGGAAAATT CTGTCCCCCG ATACATGGGC AGTCAGGGAA ACAAGCCAAT ATGGAGTAAC TCAACCTAAG GGCCTCCATG GCCACTAGGA

Figure 1e

| | | | | | | | | | |
|---|---|---|---|---|---|---|---|---|---|
| 57.1 6.5 | GGATGGGGTG | GAGCTACCGG | AAATTCGTGC | CTTATGCAAA | TGAGACACCC | AGCCCTCATC | AGTTTCTTGT | AAAAGCCTTT | GCATTCAGCT | GTAAAAATGG |
| | 5010 | 5020 | 5030 | 5040 | 5050 | 5060 | 5070 | 5080 | 5090 | 5100 |
| 57.1 6.5 | CAACCATCTT | CCAAGCCCCC | TCTCTGCAGG | GGAGAGCTTT | CTTCTTTTGC | TTATTAAACT | TTTGCTCCAA | CCTCACCCTT | TGTATCCACG | CTCCCTTAATT |
| | 5110 | 5120 | 5130 | 5140 | 5150 | 5160 | 5170 | 5180 | 5190 | 5200 |
| 57.1 6.5 | CTCTTGGTGG | TCAGACAAAT | AACTCCAGGT | AACACCTCAC | AAGGAGAGAC | TGAGAGGCTG | CTACGTTGTG | GTGCATTGGC | AAGACTAACA | AACTGGCTAG |
| | 5210 | 5220 | 5230 | 5240 | 5250 | 5260 | 5270 | 5280 | 5290 | 5300 |
| 57.1 6.5 | TGGGACATGC | ACACTTGCTT | GGTAGACATA | TATGTAGATC | TTCAGCTCTG | ACTAATGAAG | GAATACCAAA | AATCTCATAA | AAGAAAAAAA | TATTATTTGA |
| | 5310 | 5320 | 5330 | 5340 | 5350 | 5360 | 5370 | 5380 | 5390 | 5400 |
| 57.1 6.5 | GCTTTGTTTT | GTGGTGTAAG | TGGGGAGCCCC | ACAGGCACCC | AGGATAGGAG | AGCTTTGCTC | AGAATCCAAG | CTGACTGAAT | CTTTCCCTGG | GCCAGCCCAA |
| | 5410 | 5420 | 5430 | 5440 | 5450 | 5460 | 5470 | 5480 | 5490 | 5500 |
| 57.1 6.5 | GAATGAGACT | AAGCTGATTG | AGGAGCCTGG | TGCCTCCTGG | CAAGAAAGCC | TGTCTGACAC | CTGACTATCC | AGAAGTCACA | GCTACTGAAT | ATTGAGACTT |
| | 5510 | 5520 | 5530 | 5540 | 5550 | 5560 | 5570 | 5580 | 5590 | 5600 |
| 57.1 6.5 | GAAACAGAGA | GAGAGAGAGA | GAGAGAGAGA | CACACAGAGA | GAGAGAGAGA | GAGAGAGAGA | CACACAGAGA | GAGAGAGAGA | GAGAGAGAGA | GAGAGAGAGA |
| | 5610 | 5620 | 5630 | 5640 | 5650 | 5660 | 5670 | 5680 | 5690 | 5700 |
| 57.1 6.5 | TCTGATTTGA | AAAGCAGAAT | TCTGCTGGGG | GCTTGTTAAA | TGCAGAGTTT | CTGATACAGT | AGGTCCAGGC | CAGGCCCTGA | AGATTGCATA | TCTAAGTTCC |
| | 5710 | 5720 | 5730 | 5740 | 5750 | 5760 | 5770 | 5780 | 5790 | 5800 |
| 57.1 6.5 | CAGGTGATGC | CAATGCTGCT | TCCCCCAGGA | CCACACTTTG | AGAACCACCA | CCCTAAGGCA | ATCTGTGTTG | GTTTCTAATA | TCAGAAGAGG | GCTGGGAGTG |
| | 5810 | 5820 | 5830 | 5840 | 5850 | 5860 | 5870 | 5880 | 5890 | 5900 |
| 57.1 6.5 | GGCTGGGAGG | CAGAGGTGTA | GGATCAGTGA | GACCACACCT | GACCCACCCT | GGACCAGCTCC | CCACCCCAAT | CTTGCCAGCAT | TTTATTTCCT | GGGAGTCCTG |
| | 5910 | 5920 | 5930 | 5940 | 5950 | 5960 | 5970 | 5980 | 5990 | 6000 |

Figure 1f

| position | sequence |
|---|---|
| 57.1 6.5 6010 | GGAATGGAAG ACACCCAGGA AGGGACCAGA AGGGACCAAA TGTGGGGTCA CAGGGTGATC CAGGGTGATC GCTTCATACA GCACCTGGGG CTCCCGCCAC TCCACAACTG 6100 |
| 57.1 6.5 6110 | GCCCCCACAC CCTCAGTCTT CCCACCCCTC ACGACACTGA CCTCCAGACC TTCCTCGACT GCTCTCAGCA GGTTGGGCCT GGGATGTGAC ACTAGGAGCT 6200 |
| 57.1 6.5 6210 | CTGAGTGTAC CTTCTGATCC AAAGATAGGG TGACTGCGTA TGACAAGTAC TCAGAAGTGGGC CATTAATAAG ACCTTGAACA TTGGCAAAAT GGCTTCAGTC 6300 |
| 57.1 6.5 6310 | ACGTGTGCTT GAGAATTCCA GTGTTTTCTA GATATGGCAT CCATGAGCCC ACACAAACAC TGGAGGGCGT CGTGAGCATA CTGAAACCCA TAACTGCTGC 6400 |
| 57.1 6.5 6410 | ACTGGATCC |

Figure 1g

METHOD FOR DETERMINING ANCESTRAL HAPLOTYPES USING HAPLOSPECIFIC GEOMETRIC ELEMENTS WITHIN THE MAJOR HISTOCOMPATIBILITY COMPLEX MULTIGENE CLUSTER

CROSS REFERENCE TO RELATED APPLICATION

The present application is a continuation of application Ser. No. 08/893,971, filed on Jul. 16, 1997 now abandoned, which is a continuation of application Ser. No. 08/232,229, filed on Aug. 3, 1994, now abandoned, which is the national stage application filed under 37 CFR 371 from PCT/AU92/00583 filed on Oct. 30, 1992.

BACKGROUND OF THE INVENTION

This invention broadly relates to the field of molecular genetics. More specifically, the invention relates to methods for genetic analysis of DNA sequences corresponding to ancestral haplotypes of multigene complexes such as the Human Major Histocompatibility Complex and fragments thereof.

The Human Major Histocompatibility Complex (MHC) is a region of chromosomal DNA which plays a key role in the immune system and influences diverse functions and diseases. The MHC contains multiple polymorphic and duplicated genes (Zhang et al, 1990). At the centromeric end of the human chromosome on which the MHC is found there are genes such as HLA DR, DQ and DP which encode the Class II products involved in specific antigen presentation. At the telomeric end of the chromosome there are multiple genes.uch as HLA-A, B and C which encode the Class I products recognised by cytotoxic T cells. In the central region there are genes for amplifiers and mediators such as C4, C2, Bf and tumour necrosis factors (TNF-a, TNF-b), together with a heterogeneous collection of at least ten other genes (Sargent et al, 1989; Spies et al, 1989). Although only some of these genes have been sequenced it is already obvious that there is no single gene family, in that the products vary substantially in their structure. Genes such as heat shock protein 70 may possibly have a role in antigen processing prior to presentation. The products of some of the other genes may possibly be involved in intercellular adhesion, and perhaps some could influence immune responses as accessory molecules (Banerji et al, 1990). The B144 gene, together with the complement and TNF genes, could possibly play a role in the regulation of antibody production (French and Dawkins, 1990). Although more detailed information is required, it is possible that the MHC could be thought of as a chromosomal region containing heterogeneous genes which in various ways regulate and direct immunological responses, whether mediated by antibody, T cells or other effector mechanisms.

For many years it has been known that the MHC contains genes which influence the susceptibility to many diseases (Dawkins et al, 1983). Products of the human MHC are also intimately involved in tissue rejection, wherein transplanted tissues bearing MHC products which are non-identical to the transplant recipient are recognised as foreign by the immune system and rejected.

Because of the practical importance of transplantation, much effort has been spent in "tissue typing" within the MHC to ascertain whether candidate tissues for transplantation carry the same MHC ancestral haplotype as the intended recipient. Most of this typing has been by serological analysis focusing on the DR and DQ HLA class II gene products, the HLA B class I gene products, as well as other markers.

Current tissue typing techniques are subject to a degree of ambiguity which is inherently associated with serological determinations as well as time delays associated with such analysis. There is additionally a need for further "markers" in order to assess the compatibility or otherwise of tissue for transplantation.

"Tissue typing" is also important in assessing susceptibility and resistance to disease as mentioned above. Where a patient's susceptibility to autoimmune or other diseases can be detected at an early stage, appropriate therapeutic regimes, and counselling can be implemented before disease progression with attendant advantages.

Ancestral haplotypes are DNA sequences from multigene complexes such as MHC. The ancestral haplotypes of the MHC extend from HLA B to HLA DR and have been conserved en bloc. These ancestral haplotypes and recombinants between any two of them account for about 73% of ancestral haplotypes in our caucasian population. The existence of ancestral haplotypes implies conservation of large chromosomal segments. These ancestral haplotypes carry many MHC genes, other than the HLA, which may be relevant to antigen presentation, autoimmune responses and transplantation rejection. Tissue typing is an analysis of the combination of alleles encoded within the MHC. Many of these allelic combinations can be recognised as ancestral haplotypes. Other multigene complexes containing ancestral haplotypes include the lipoprotein gene complex and the RCA complex This invention stems from characterisation of DNA corresponding to ancestral haplotypes. The inventors have surprisingly found that the DNA sequences corresponding to a particular ancestral haplotype are identical within that ancestral haplotype, whereas DNA sequences between ancestral haplotypes are very polymorphic. Each ancestral haplotype, therefore, possesses a unique nucleotide sequence which can be exploited in assigning ancestral haplotypes. Accordingly, genetic analysis and assignment of ancestral haplotype maybe readily conducted according to the methods of this invention. This is particularly important where identity at the genomic sequence level may be necessary for the most desirable outcome following grafts and transplants such as in bone marrow grafting (Christiansen et al, 1991). The genetic analysis of the present invention provides the ability to "match" ancestral haplotypes between individuals or to "type" ancestral haplotypes by a comparison to a reference panel of ancestral haplotypes.

DESCRIPTION OF THE INVENTION

In accordance with the first aspect of this invention, there is provided a method for genetic analysis comprising comparing a first DNA sequence corresponding to an ancestral haplotype or recombinant thereof of a multigene complex, such as the MHC, with one or more reference DNA sequences each corresponding to a separate ancestral haplotype so as to establish identity or non-identity there between and thus an assignment of ancestral haplotype of said first DNA sequence.

DNA sequences which may be compared in assigning ancestral haplotype may comprise the DNA sequence of any multigene complex such as but not limited to the lipoprotein gene complex, the RCA complex and the MHC complex. Preferably the multigene complex is the MHC such as HLA C between HLA B and TNF+B144, and/or a DNA sequence corresponding to one or more haplospecific geometric elements of the human Major Histocompatibility Complex as defined hereinafter.

The present invention is directed to genetic analysis of the genomes of higher organisms such as from mammals, plants and insects. Preferred mammals are humans, livestock animals, companion animals and wild animals. Most preferably, the mammal is a human.

DNA sequences corresponding to ancestral haplotypes or recombinants thereof may be readily analysed by a number of techniques such as DNA sequence analysis, restriction fragment length polymorphism (RFLP), reaction with haplospecific oligonucleotide probes, heteroduplex analysis, primer directed amplification and other methods as are well known in the art. The genome itself may be subject to the analysis or via cDNA or mRNA.

In a preferred aspect of the present invention, the comparison is by the use of oligonucleotide probes which may also be labelled with a reporter molecule or a primer to direct amplification.

According to this preferred aspect, there is provided a method for matching a particular ancestral haplotype in the genome of two or more individuals of a higher organism, said method comprising contacting a region of the genome or fragment or portion thereof from each individual with an oligonucleotide probe which hybridises to at least one complementary sequence within the ancestral haplotype and comparing the extent of hybridisation to match the non-identity or identity of the ancestral haplotype.

Another preferred aspect of the present invention provides a method for matching a particular ancestral haplotype in the genome of two or more individuals of a higher organism, said method comprising contacting a region of the genome or fragment or portion thereof from each individual with at least one oligonucleotide primer which hybridises to at least one complementary sequence within the ancestral haplotype and comparing the profile of hybridisation or genomic amplification products, or nucleotide sequence of such amplification products to match the non-identity or identity of the ancestral haplotype.

Yet another preferred aspect of the present invention provides a method wherein the oligonucleotide probe hybridises to multiple complementary sequences within the ancestral haplotype.

A DNA sample may be isolated from an individual and then subject to characterisation as detailed above to assign ancestral haplotype. For example, a DNA sample may be isolated and analysed for specific hybridisation with an ancestral haplotype specific probe as provided according to this invention.

Alternatively, ancestral haplotype sequences within a DNA sample may be amplified, for example, using conventional techniques such as linear amplification using a single primer which hybridises to ancestral haplotype sequences, or by amplification using paired primers. Amplified sequences may then be detected directly by visual analysis of separated fragments or by reaction with ancestral haplotype specific or non-ancestral haplotype specific probes.

By ways of further example, a DNA sample from an individual may be reacted with one or more restriction endonucleases, the resultant fragments separated, for example by gel electrophoresis, followed by subsequent analysis of restriction fragments using a relevant MHC specific probe by Southern analysis (Sambrook et al., 1989). Resulting restriction fragment patterns may then be compared with restriction fragment patterns prepared from reference samples of known ancestral haplotypes. By a comparison of restriction fragment polymorphisms with reference samples, a designation of ancestral haplotype may be made. This is possible by virtue of the absolute conservation of ancestral haplotype sequences within a specific ancestral haplotype.

By a comparison of ancestral haplotype nucleotide sequences, the inventors have surprisingly identified polymorphic regions within the ancestral haplotype which comprises stable stretches of nucleotides which differ between ancestral haplotype. Preferably, these polymorphic regions are haplospecific geometric elements (HGEs).

There are approximately 50 ancestral haplotypes selected in the human caucasoid population, with each ancestral haplotype possessing Haplospecific Geometric Elements. The HGEs are geometric in that there is a mathematical relationship between the number of bases which is a characteristic of each ancestral haplotype. There is also geometry in the sense that there is a symmetry around the center of the region which is defined from the boundaries which are more or less common to different ancestral haplotypes. HGEs are also distinctive in that there is non-random usage of nucleotides with iteration of certain components of the sequence. While these components may contain simple sets (eg di and trinucleotide iterations), these do not themselves define the elements and do not allow recognition of haplospecificity or geometric patterns.

As will be described hereinafter, HGEs have been shown to occur at various sites within the MHC. Elements at each of these sites may be related to each other in that they have the same or predictable geometry.

It should be appreciated that the detection of HGEs, and indeed the characterisation of DNA sequences corresponding to ancestral haplotypes or recombinants thereof are not dependent upon the use of any specific technique. As described herein, a variety of techniques can be used for identification and characterisation of ancestral haplotype specific sequence sequences.

While HGEs are characteristic of each individual ancestral haplotype, and characterisation thereof therefore provides direct information as to ancestral haplotype, nucleotide sequences outside of the HGEs may also be utilised to distinguish between ancestral haplotypes. The inventors have discovered that ancestral haplotype sequences differ from one another along their length notwithstanding that marked variation occurs within HGEs. Accordingly, the nucleotide sequence of different ancestral haplotypes may be ascertained and the respective differences thereberween used to construct polynucleotide probes which discriminate between ancestral haplotypes. Preferably, the probes hybridize to complementary sequences in a region flanking the HGE and will hybridize to complementary sites represented at least twice.

In accordance with an aspect of this invention, there is provided a method for genetic analysis which comprises the steps of:
(a) hybridising one or more polynucleotide primers having complementary nucleotide sequence to nucleotide sequences flanking HGEs with a sample containing a DNA sequence corresponding to a multigene complex such as the MHC;
(b) amplifying HGEs within multigene complex by multiple cycles of primer extensions; and (c) detecting the amplified products resulting from primer extension of the HGEs, which products are characteristic of ancestral haplotypes or recombinants thereof.

Single primer sequences may be utilised for amplification (such as linear amplification) whereafter amplified products may be detected by hybridisation with probes complementary in sequence to said amplified HGE.

Paired nucleotide sequences flanking HGEs may be used to amplify the HGEs following multiple cycles of primer extension. Amplified products may be detected by direct visual analysis after fractionation on a gel or other separation medium.

HGEs, or indeed other regions of the ancestral haplotype of the human MHC may be amplified by direct amplification of single stranded RNA or denatured double stranded DNA. Such methods, which employ T7 RNA polymerase to produce large numbers of copies from each template molecule are described by Compton, 1991.

In accordance with a further aspect of this invention, there is provided a method for the detection of ancestral haplotype which method comprises the steps of:

(a) comparing nucleotide sequences of one or more ancestral haplotypes to ascertain polymorphisms between said ancestral haplotype sequences;

(b) constructing polynucleotides from any sequence region between ancestral haplotype sequences which will discriminate between different ancestral haplotypes;

(c) utilising said polynucleotides of step (b) to detect an ancestral haplotype of a multigene complex such as the MHC from the genome of a higher organism sample by hybridising said polynucleotide to said genome and thereafter detecting polynucleotide binding or absence thereof.

In this method, polynucleotides may be used to amplify selected sequences of ancestral haplotypes, the production of amplified sequences corresponding to ancestral haplotype identification.

The aforementioned HGEs have particular utility as surrogate markers for HLA B. HGEs are proximal to HLA B on the MHC lying some 30 to 50 kilobases towards the centromeric end of human chromosome 6. Accordingly, characterising HGEs allows a direct inference as to the ancestral haplotype at the HLA-B locus. Given that recombination in between HGEs and the HLA B would be expected to be a rare event, the assignment of an ancestral haplotype based on characterisation of the HGE, particularly within the CL-1 locus, should hold true for the HLA Ballele, except for the situation where recombination takes place between the HGEs and the HLA B allele.

In a preferred aspect of the present invention, there is provided a method for identifying a ancestral haplotype in the genome of an individual of a higher organism, said method comprising amplifying the ancestral haplotype or portions thereof using a primer capable of hybridising to complementary sequences represented at least once within the ancestral haplotype and comparing the resultant amplication products with a reference of amplication products from a known ancestral haplotype using substantially the same primer to thereby establish identity or non-identity therebetween.

In accordance with a further aspect of this invention, there is provided a method for surrogate typing at the HLA B allele, which method comprises characterising the nucleotide sequence of a HGE.

The nucleotide sequence of HGEs may be carried out by methods well known in the art for the characterisation of any nucleotide sequences.

In accordance with a still further aspect of this invention, there is provided a method for genetic analysis which comprises the steps of:

(a) digesting a DNA sample corresponding to a first human ancestral haplotype or a recombinant thereof with one or more restriction endonucleases, which restriction endonucleases do not cleave within the HGEs of a multigene complex such as the MHC;

(b) separating and analysing the DNA restriction fragments so produced, and comparing the same with one or more reference samples comprising ancestral haplotypes of known ancestral haplotype or recombinants thereof cleaved with said one or more restriction endonucleases of step (a) so as to establish identity or non-identity therebetween.

In accordance with yet another aspect of this invention, there is provided genomic DNA corresponding to an ancestral haplotype of a multigene complex such as the MHC or a fragment thereof. By way of exanple, there is provided genomic DNA corresponding to ancestral haplotypes 57.1, 7.1, 8.1, 18.2, 46.1 and 62.1 of the MHC. These ancestral haplotypes are representative of approximately 50 ancestral haplotypes of which about 22 represent approximately 72% of ancestral haplotypes of the human MHC in a caucasoid population. Following the methods of this invention, any ancestral haplotype genomic DNA or fragment thereof may be isolated utilising hybridisation probes which recognise common sequences between ancestral haplotypes. For example, such conserved sequences flank HGEs.

This invention provides in a particular aspect a genomic DNA sequence corresponding to a fragment of ancestral haplotype 57.1 having a nucleotide sequence as set forth in FIG. 1. This invention also includes unique fragments of such sequence which would generally comprise in excess of 30 to 50 nucleotides. It is to be appreciated that searches can be readily conducted through DNA data bases to establish uniqueness of fragments which are characteristic of ancestral haplotypes. This aspect of the invention further extends to protein products encoded by one or more genes encoded by said nucleotide sequence. Protein products encoded by said one or more genes or fragments thereof may have particular utility as therapeutic immunoregulatory agents, and are included within the scope of the present invention.

In another aspect this invention relates to a HGE of a multigene complex such as the MHC.

HGEs of characteristic nucleotide sequence are carried by each ancestral haplotype. As a consequence, HGEs are characteristic of each ancestral haplotype of, for example, the MHC. As previously mentioned, HGEs possess geometry in the sense that there is a symmetry around the centre of the region which is defined from the boundaries which are more or less common to different ancestral haplotypes. HGEs are also distinctive in that there is non-random usage of nucleotides with iteration of certain components of the sequence, namely di and trinucleotide iterations.

HGEs are characterised by possessing conserved sequences at their boundaries and a variant number of di and trinucleotide repeats in the central region.

Examples of HGEs have the following sequences:

TABLE 1

| | | | | number of variable nucleotides |
|---|---|---|---|---|
| 57.1 – CL1 | X T C A G A | (T C)$_{12}$ (T G)$_6$ (T C)$_{14}$ (T G)$_3$ (T C)$_{12}$ | T G T T T Y | 94 |
| 18.2 – CL1 | X . . . . . | (T C)$_{14}$ | . . . . . Z | 28 |
| 8.1 – CL1 | X. . . . . | (T C)$_{28}$ | . . . . . Z | 56 |
| 7.1 – CL1 | X. . . . . | (T C)$_{15}$ | . . . . . Z | 30 |
| 57.1 – CL2 | X . . . . . | T A (T C)$_{18}$ T T (T C)$_9$ | . . . . . Z | 58 |
| 8.1 – CL2 | X . . . . . | (T C)$_{15}$ T G (T C)$_8$ T G (T C)$_8$ T G (T C)$_8$ T G (T C)$_5$ | . . . . . Z | 96 |
| 7.1 – CL2 | X . . . . . | (T C)$_{15}$ T G (T C)$_8$ T G (T C)$_8$ T G (T C)$_8$ T G (T C)$_5$ | . . . . . Z | 94 |

. = consensus sequences
X: 5' – ACAAGCCCCCAGCAGAATTCTGCTTTTCAAA
Y: 5' – CAAGTCTCAATATTCAGTAGCTGTGACTTCTGGATAGTC
Z: 5' – CAAGTCTCAATATTGAGTAGCTGTGACTTCTGGATAGTC
P: 5' – CAAGTCTCAATACTGAGTAGCTGTGACTTCTGGATAGTC It is important to appreciate that the sequences flanking HGEs are generally highly conserved between the various ancestral haplotypes. These regions thus allow polynucleotide probes to be produced which allow characterisarion of HGEs by amplification of such sequences utilising techniques well known in the art and as hereinbefore described.

In yet another aspect of this invention, there is provided a polynucleotide which allows the identification and/or amplification of HGEs of the MHC, or fragments thereof capable of hybridising to sequences flanking the HGEs of the MHC.

Polynucleotides according to this aspect of the invention may be derived from conserved sequences flanking HGEs of the MHC. The number of nucleotides comprising said polynucleotide is not of importance as long as the said polynucleotides are capable of identification and/or amplification of HGEs. This is readily ascertainable by, for example, hybridisation analysis or the detection of amplification products.

By way of example, there is provided a polynucleotide primer for the identification and/or amplification of HGEs of the MHC comprising:

```
CTREP 3    T G T A A A A C G A C G G C C A G T ↑ A C A A G
           C C C C C A G C A G A A T T C T G C T T
CTREP 4    C A G G A A A C A G C T A T G A C C ↑ G A C T A
           T C C A G A A G T C A C A G C T A C T C
``` or polynucleotide comprising said nucleotide sequence, or a fragment or derivative thereof capable of hybridising to sequences flanking the HGEs of the MHC.

Preferred primers of the present invention are those set forth below in the 5' to 3' direction:

TGTAAAACGACGGCCAGT↑ACAAGCCCCCA
GCAGAATTCTGCTT;
CAGGAAACAGCTATGACC↑GACTATCCAGA
AGTCACAGCTACTC;
ACAAGCCCCCAGCAGAATTCTGCTT;
GACTATCCAGAAGTCACAGCTACTC.

In still another aspect of this invention, there is provided a recombinant vector comprising a human ancestral haplotype, recombinant thereof or fragment thereof, such as a HGE. Recombinant vectors may comprise plasmids, bacteriophage sequences or any other DNA and/or RNA construct as are well known in the art for the maintenance and replication of nucleotide sequences in a host cell, namely a prokaryotic or eukaryotic host cell.

Recombinant vectors generally comprise a selectable marker, for example one or more genes corresponding to antibiotic or drug resistance, or one or more genes corresponding to one or more factors, such as enzymes, requisite for host cell viability. Recombinant vectors generally further comprise an origin of replication which allows for replication of said vector within a host cell, as well as one or more restriction sites to enable the introduction of desired genes or nucleotide sequences into said vector. Myriad host cells are well known in the art and are described for example in Sambrook et al. (1989).

In one specific embodiment, this invention relates to a YAC vector, as described by which comprises a genomic DNA sequence corresponding to an ancestral haplotype of the MHC, a fragment thereof, or HGE as hereinbefore described.

In still a further aspect of this invention, there is provided a human cell line homozygous for a human ancestral haplotype of the MHC.

Human cells lines homozygous for human ancestral haplotypes of the MHC may comprise immortalised lymphocytes or other immortalised human cell types. Immortalisation may be carried out, for example, by transformation with a virus, such as Epstein Barr Virus (EBV).

In yet another embodiment of the present invention, the identification of an ancestral haplotype can be accomplished by multiple priming using one primer or a set of primers. According to this aspect of the invention, there is provided a method for identifying an ancestral haplotype on the genome of an individual comprising amplifying multiple regions within said haplotype with a single primer or set of primers and comparing the amplification products with a reference panel of ancestral haplotypes or with the amplification products from another individual. Furthermore, multiple priming has been shown in the HLA delta block as shown in FIG. 13.

This invention will now be described, by way of example only, with reference to the following non-limiting Figures and Examples.

BRIEF DESCRIPTION OF THE DRAWINGS

FIG. 1A–1G shows DNA sequence of 6.5 kb Bam HI fragment of ancestral haplotype 57.1 by seven continous pages FIG. 1a through FIG. 1g.

Genomic DNA was extracted in a 341 Nucleic Acid Purification System—Genepure (Applied Biosystems Inc. Foster City, CA-ABI) from B lymphoblastoid cell lines which were grown in RPMI medium supplemented with 15% foetal calf serum.

Polyrnerase chain reactions (PCR) were performed in a 20 µl volume containing 200 ng of genomic DNA from cell lines. The reaction mixtures contained 400 µM each of DATP, dTIP, dCTP and dGTP, 2.0 mM Tris-HCl (pH8.3), 20 mM $MgCl_2$, 50 mM KCl, 50 pmol each of FAM or JOE (ABI) labelled CTREP3 and CTREP4 primers and 1.6 units of Taq DNA polymerase (Amplitaq, Cetus Corp., Emeryville, Calif.). The reaction was performed in a FTS-1 Thermal Sequencer (Corbett Research, Mortlake, NSW, Australia). DNA was denatured at 95° C. for 2 minutes followed by 35 thermocycles (95° C.-10 s, 55° C.-10 s, 72° C.-20 s).

The amplification products obtained from these reactions were analysed on the 362 fluorescent Fragment Analyzer—GENESCANNER (ABI) using a 3% SEAPLAQUE low gelling temperature agarose gel(FMC Corp, Rockland, MASS.) in 1×TBE[23], at a constant voltage of 100 volts for 8 hours. The comb was positioned 4 cm from the region scanned by the laser. ROX-labelled internal size standards (Genescan 2500, ABI) were run with each sample.

Figure 7A:
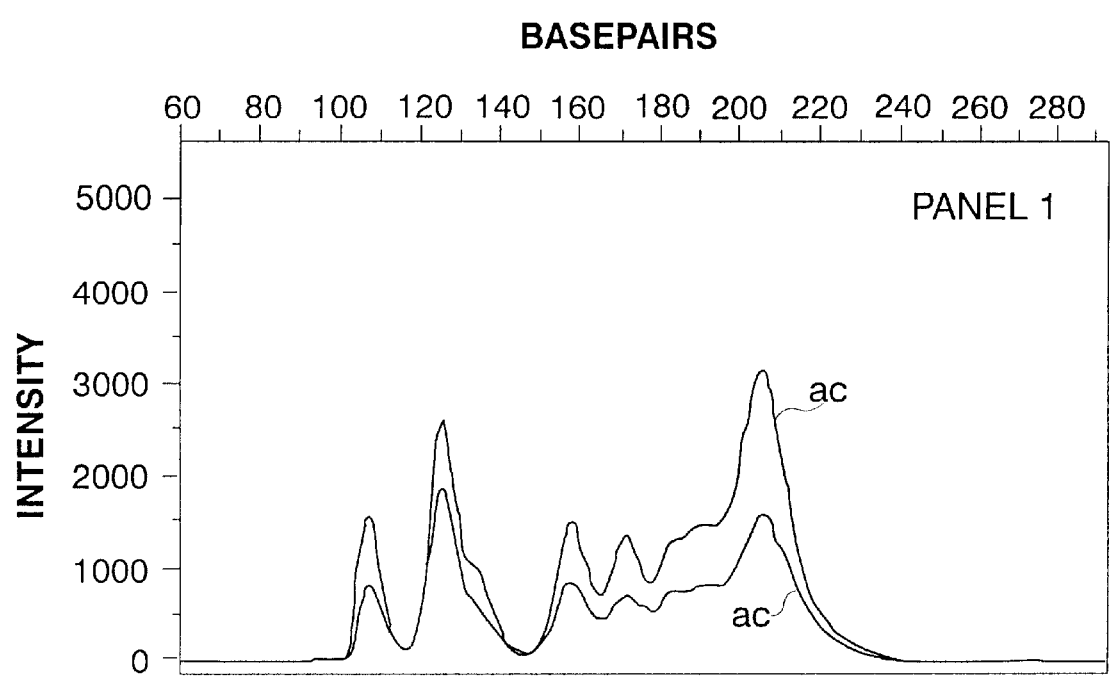
Figure 7B:
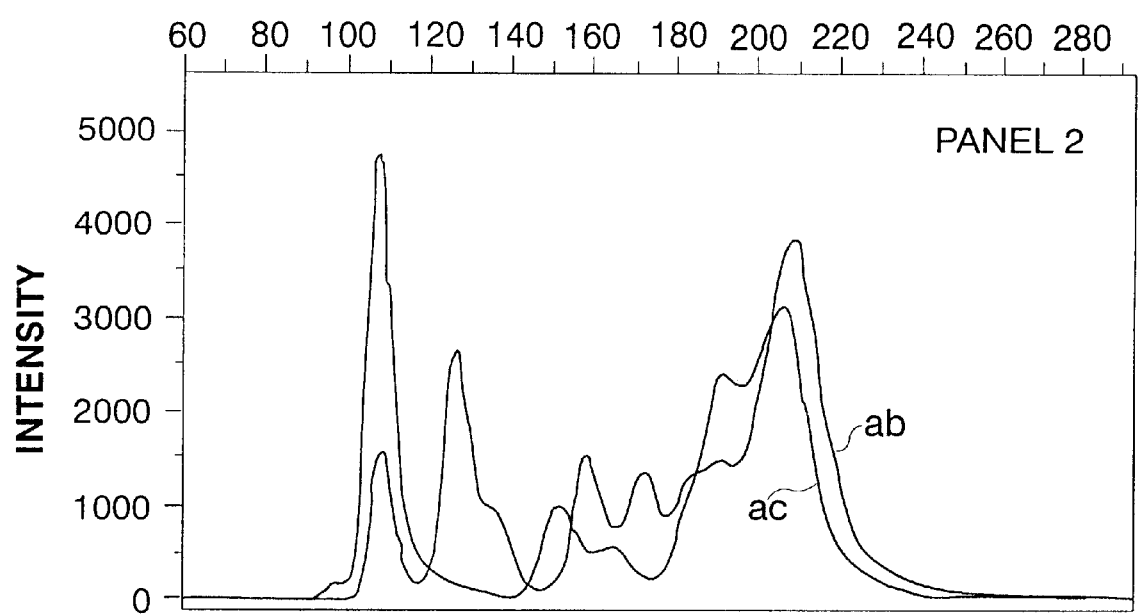
Figure 7C:
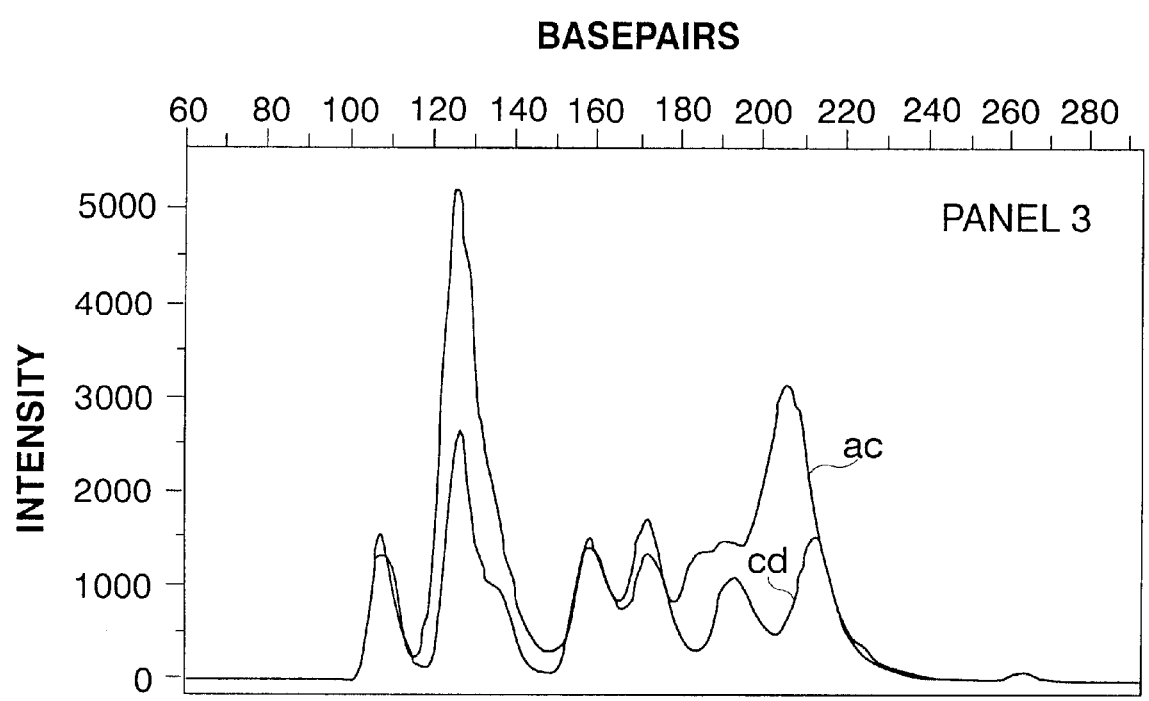
Figure 8A:
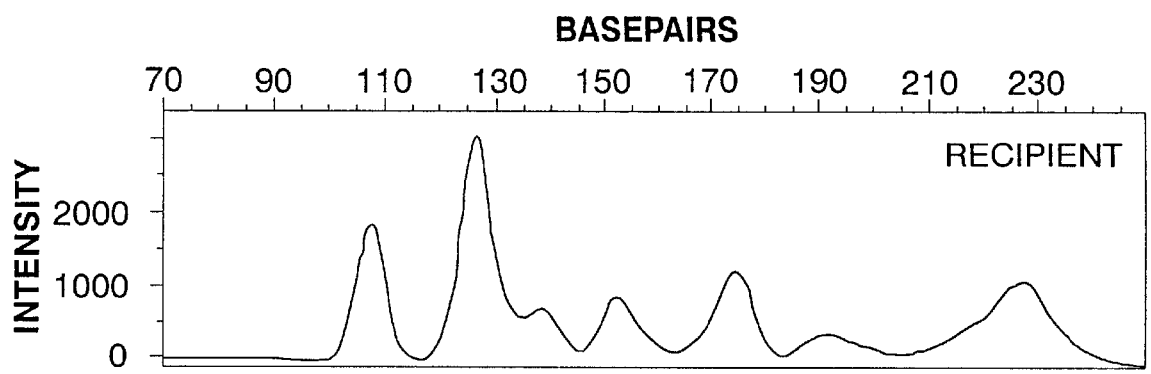
Figure 8B:
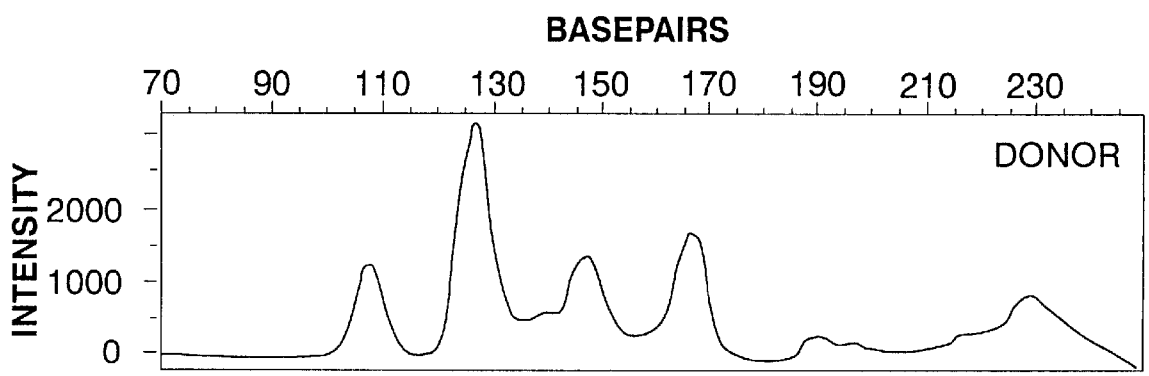
Figure 8C:
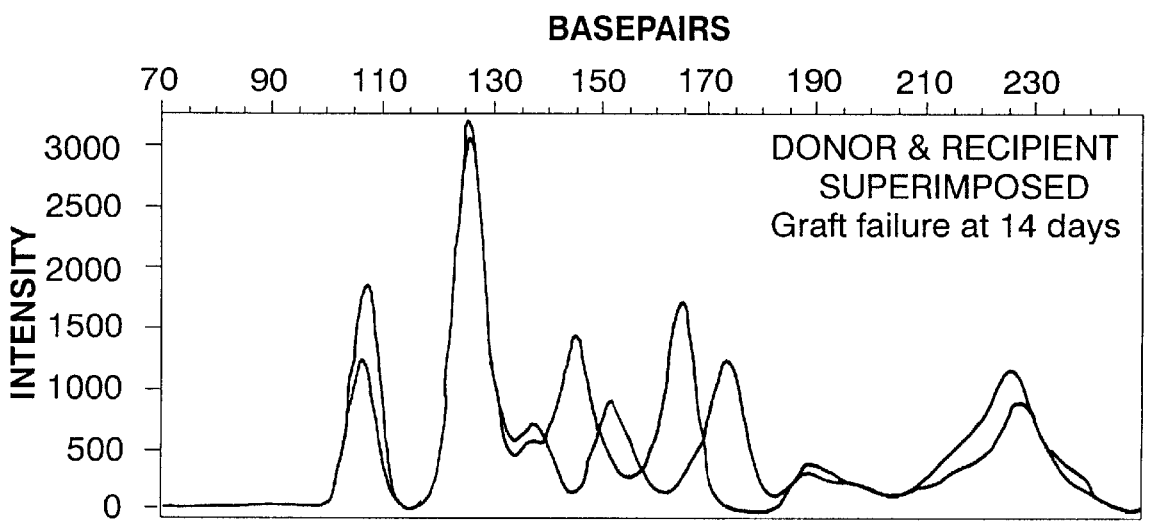
Figure 8D:
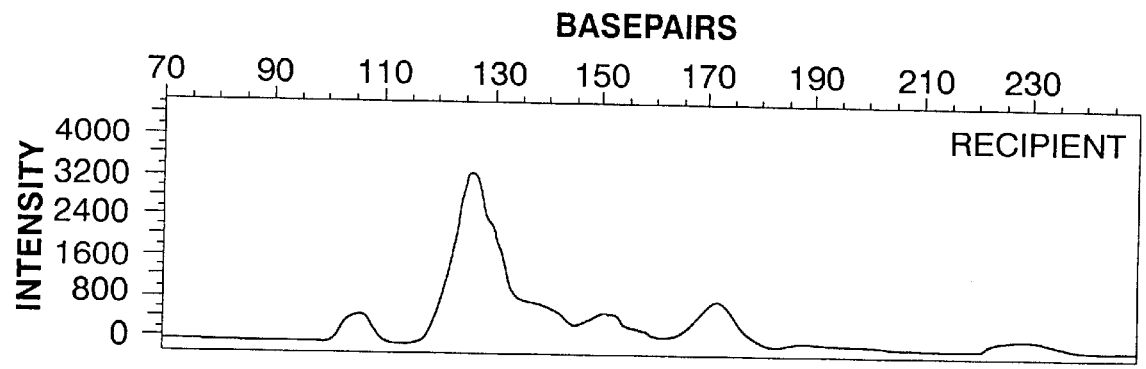
Figure 8E:
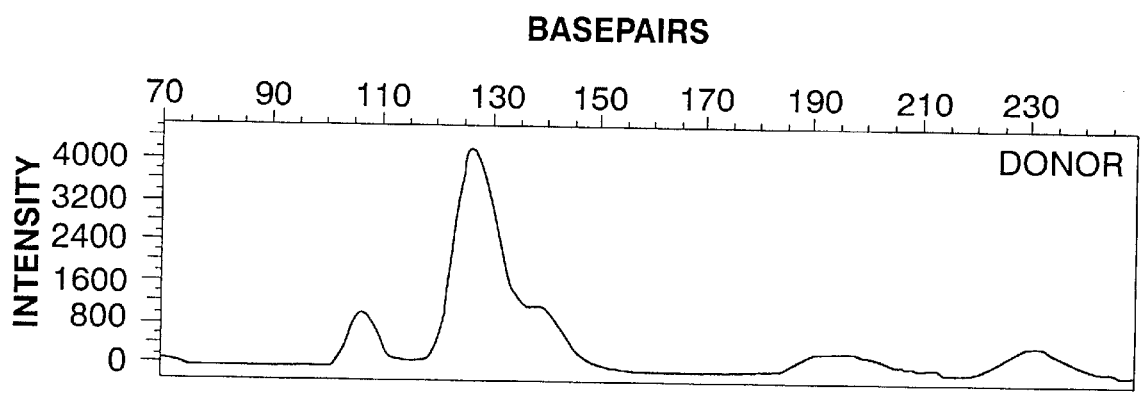
Figure 8F:
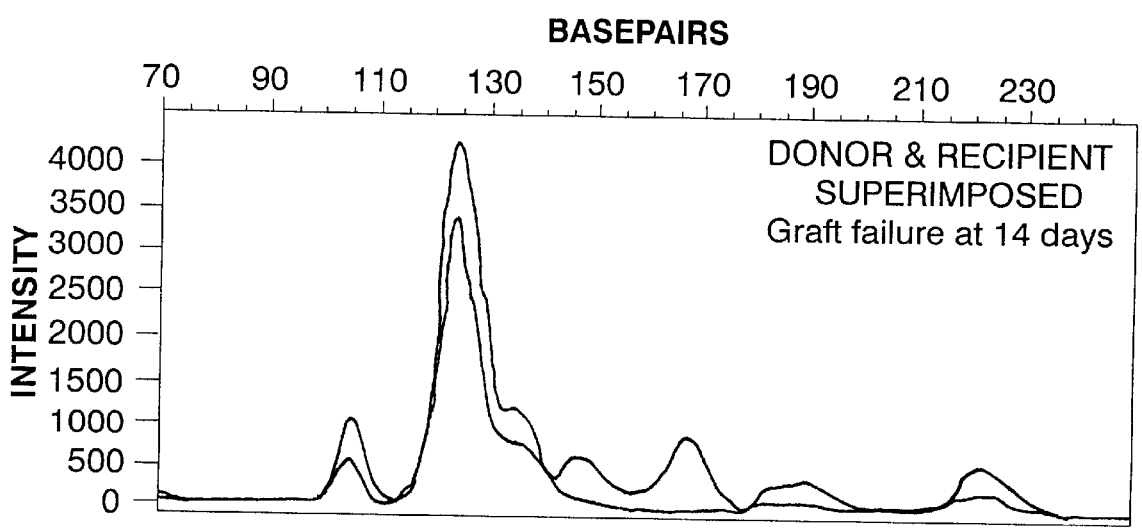
Figure 8G:
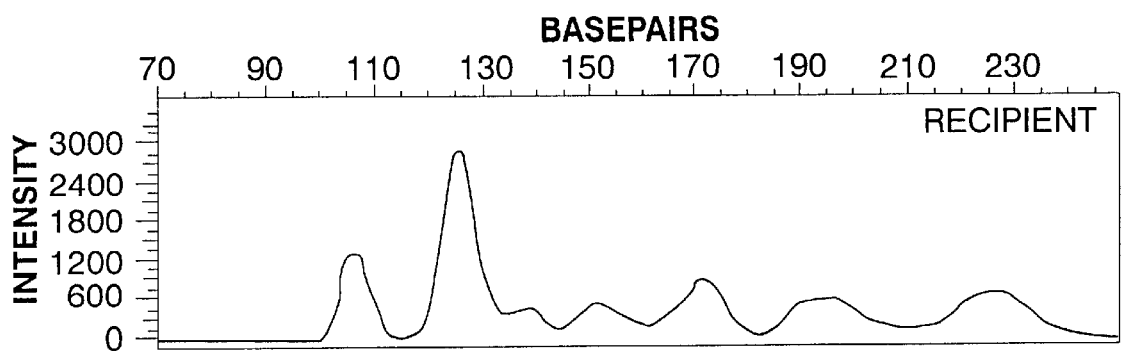
Figure 8H:
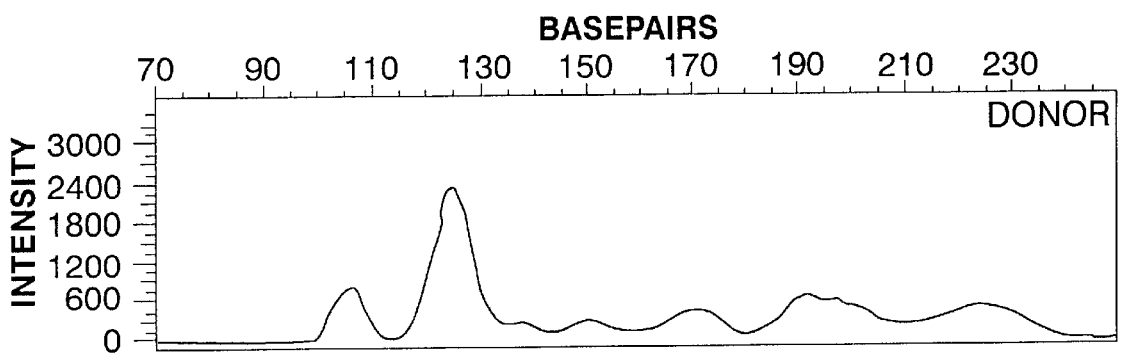
Figure 8I:
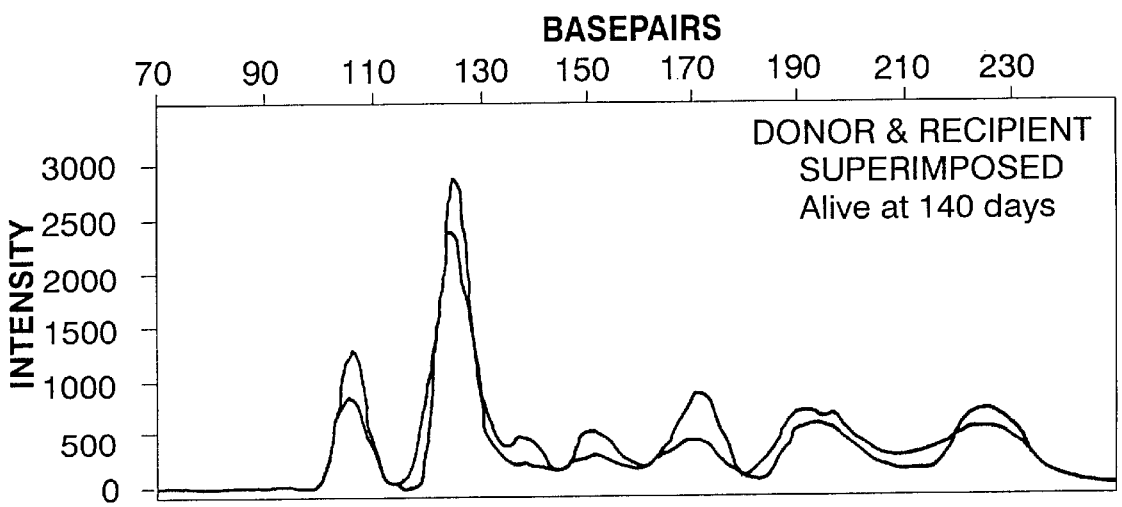
Figure 8J:
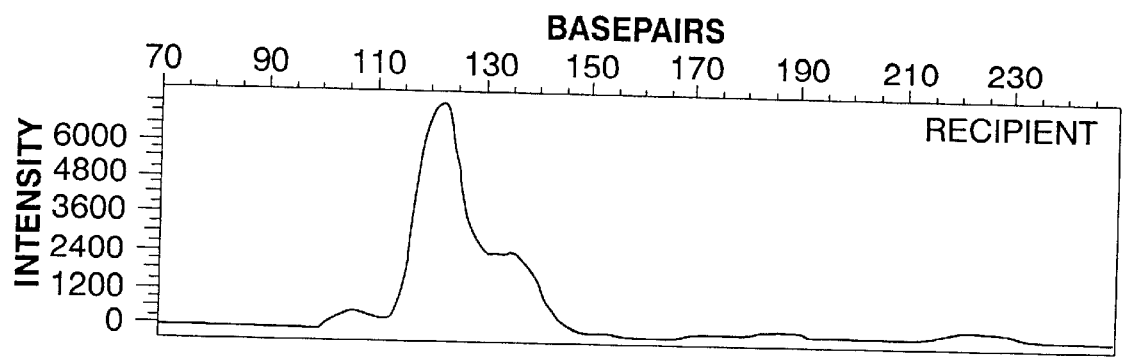
Figure 8K:
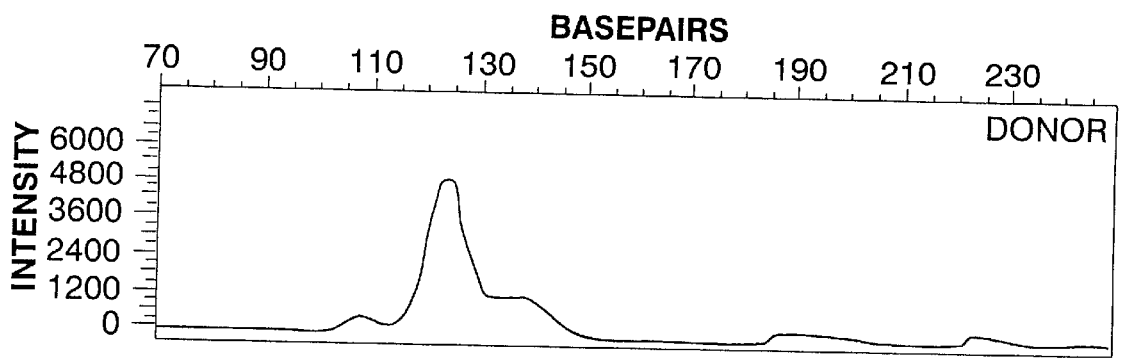
Figure 8L:
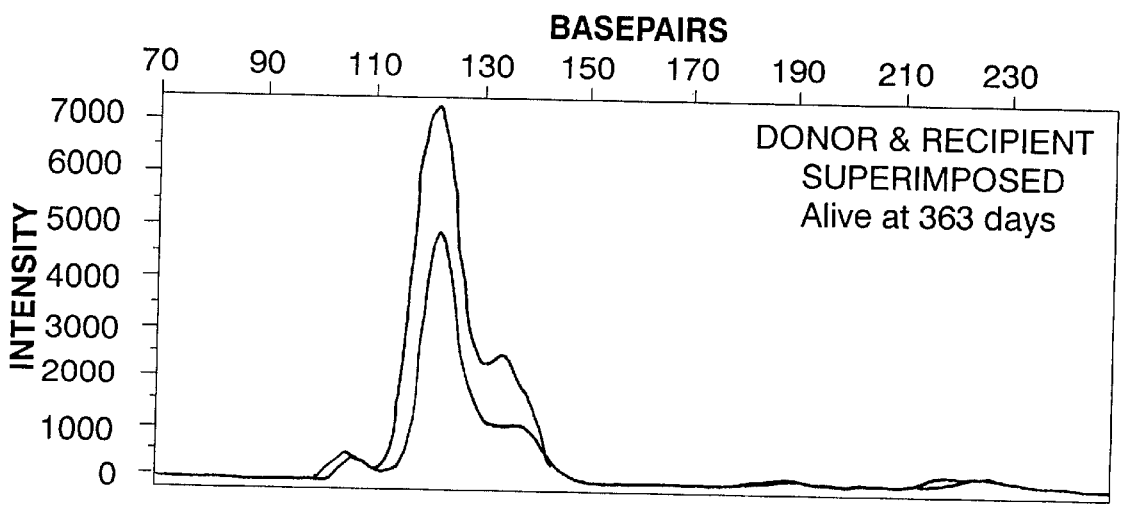
Figure 9A:
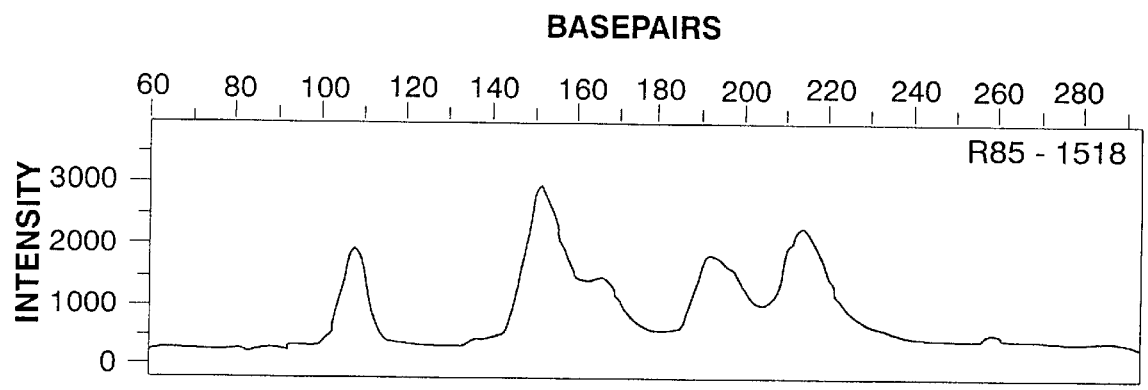
Figure 9B:
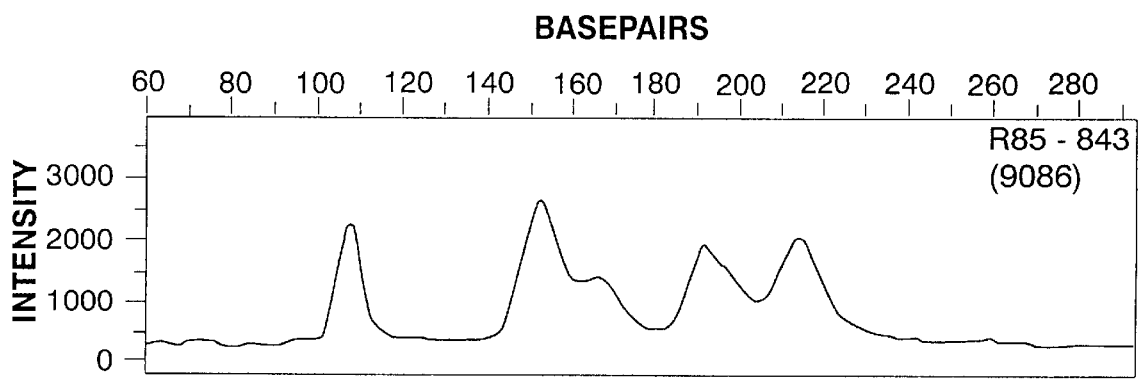
Figure 9C:
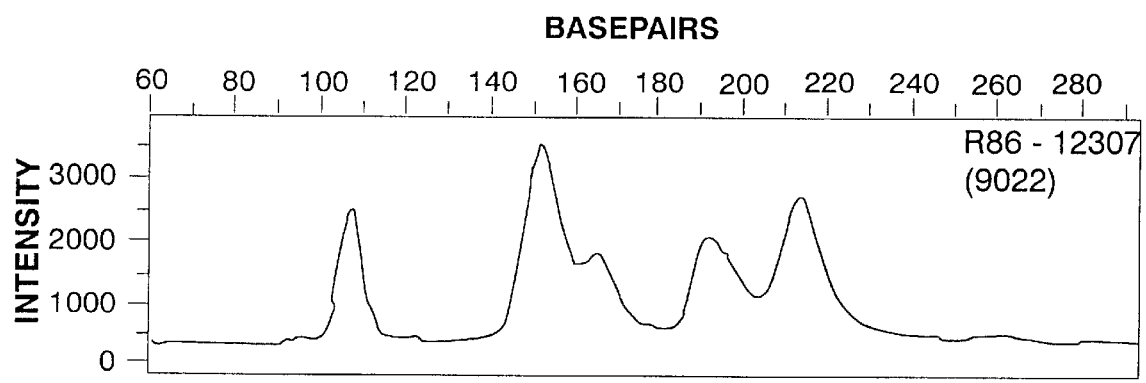
Figure 9D:
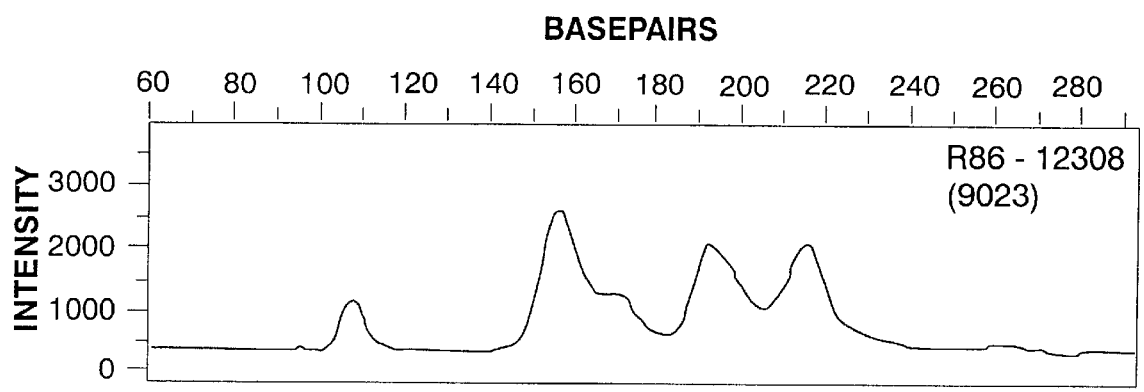
Figure 9E:
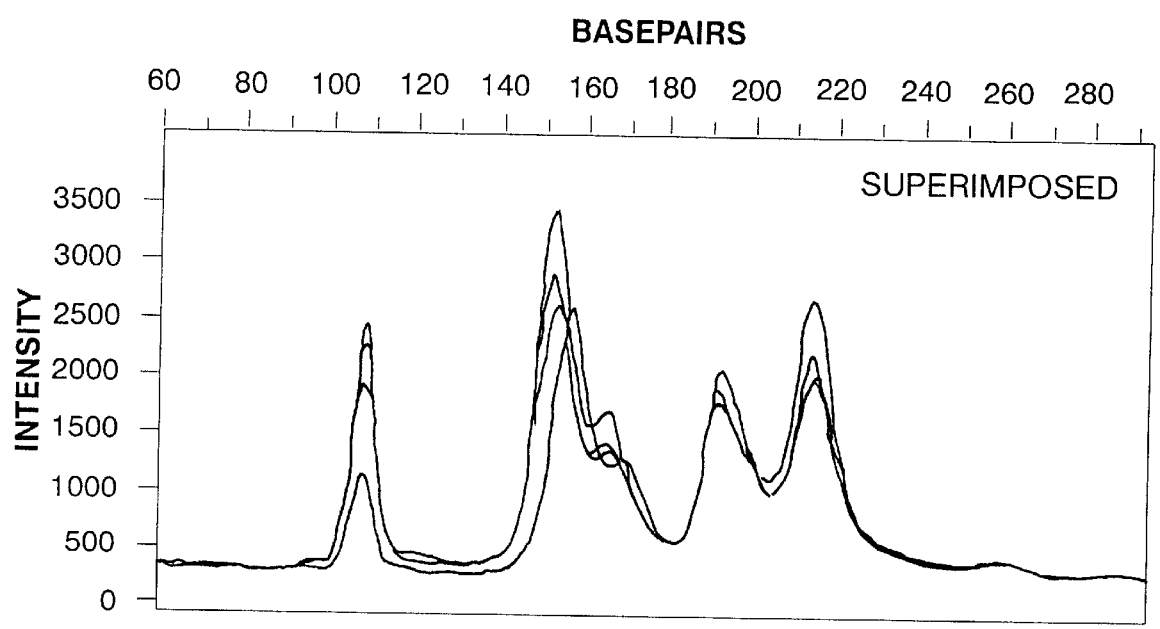
Figure 10A:
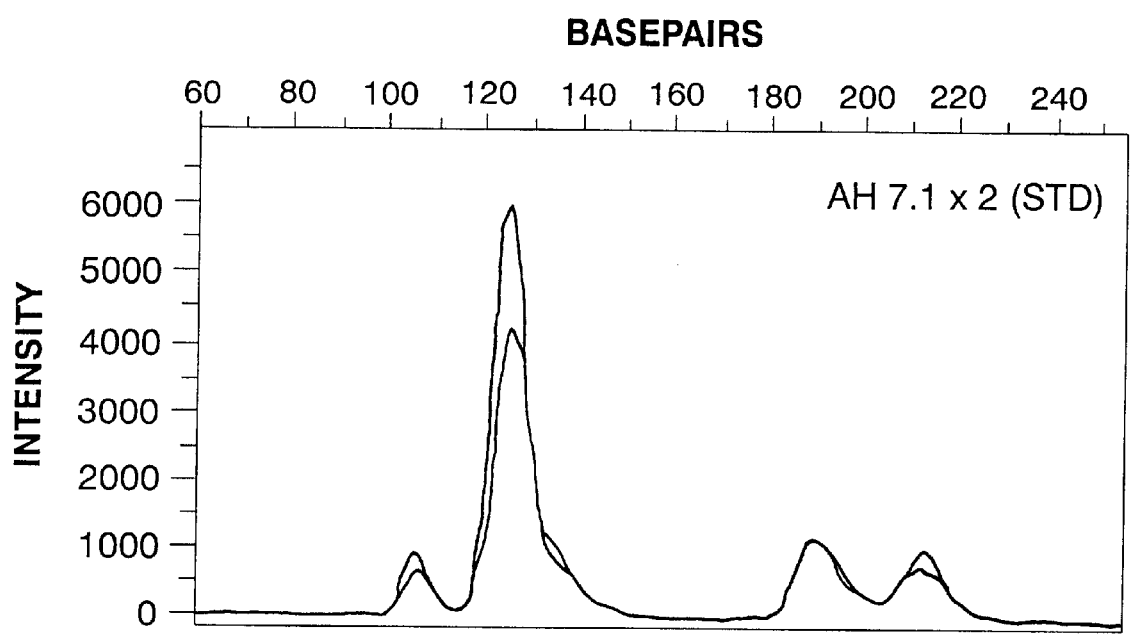
Figure 10B:
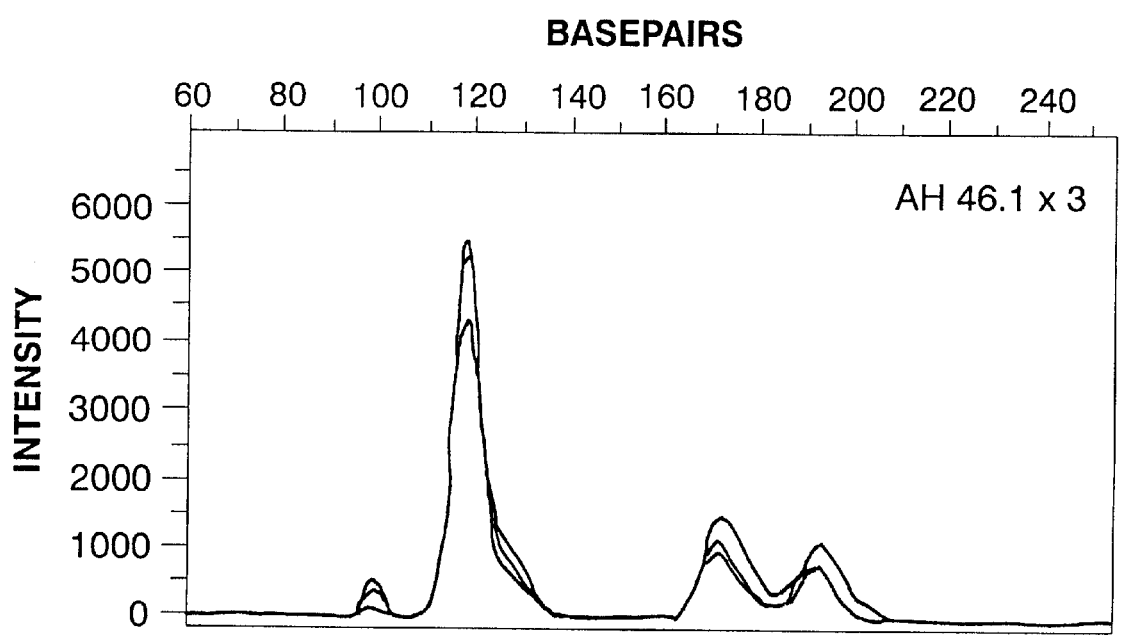
Figure 10C:
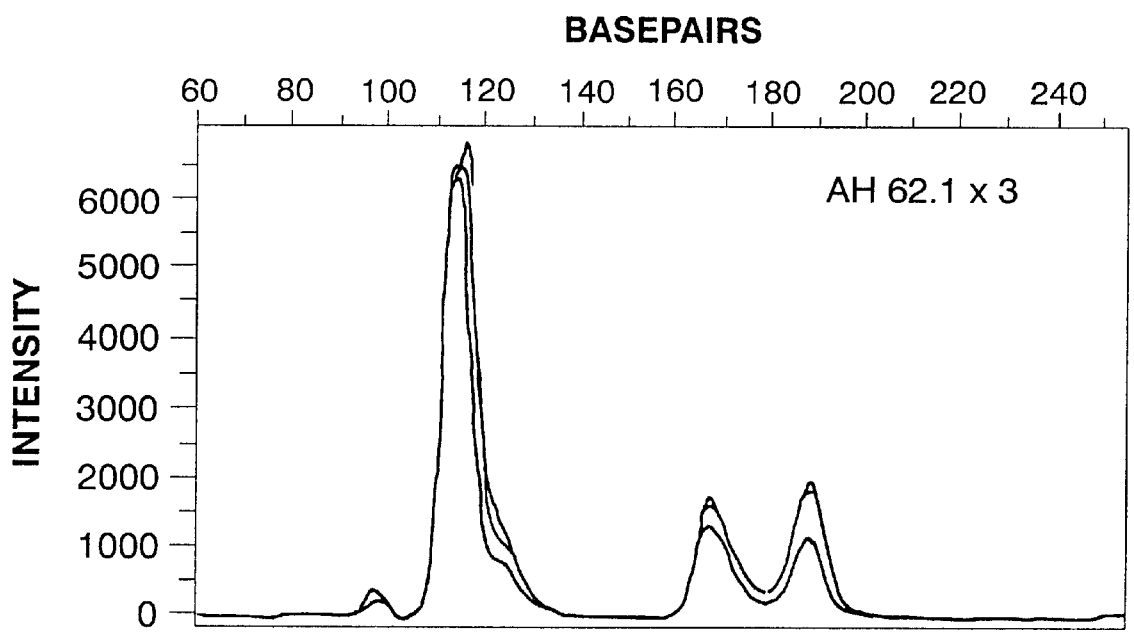
Figure 10D:
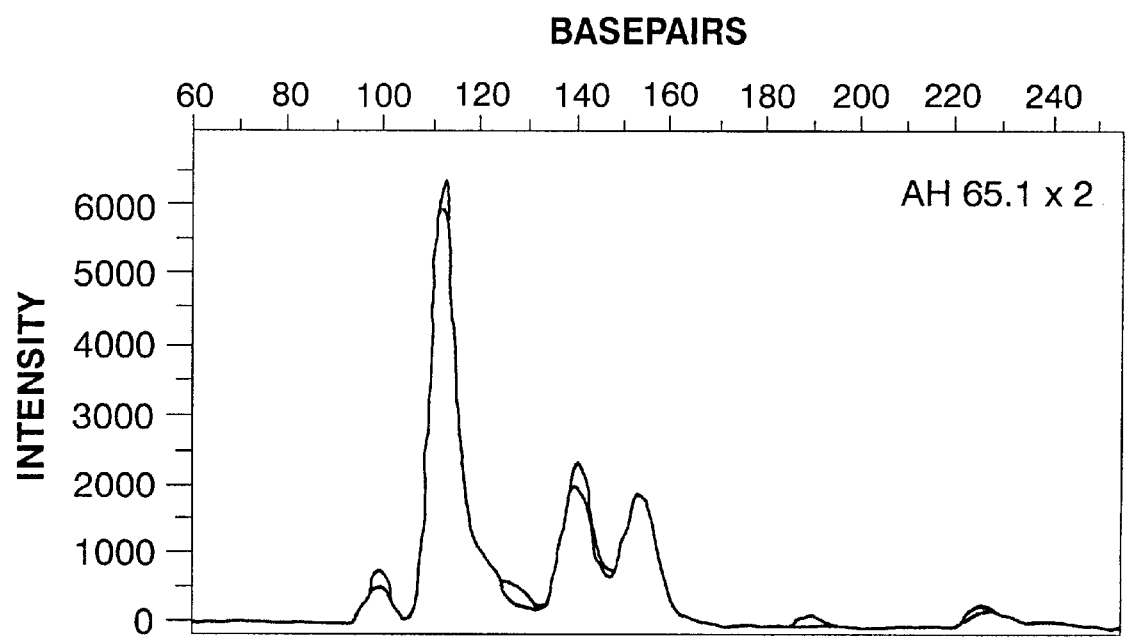
Figure 10E:
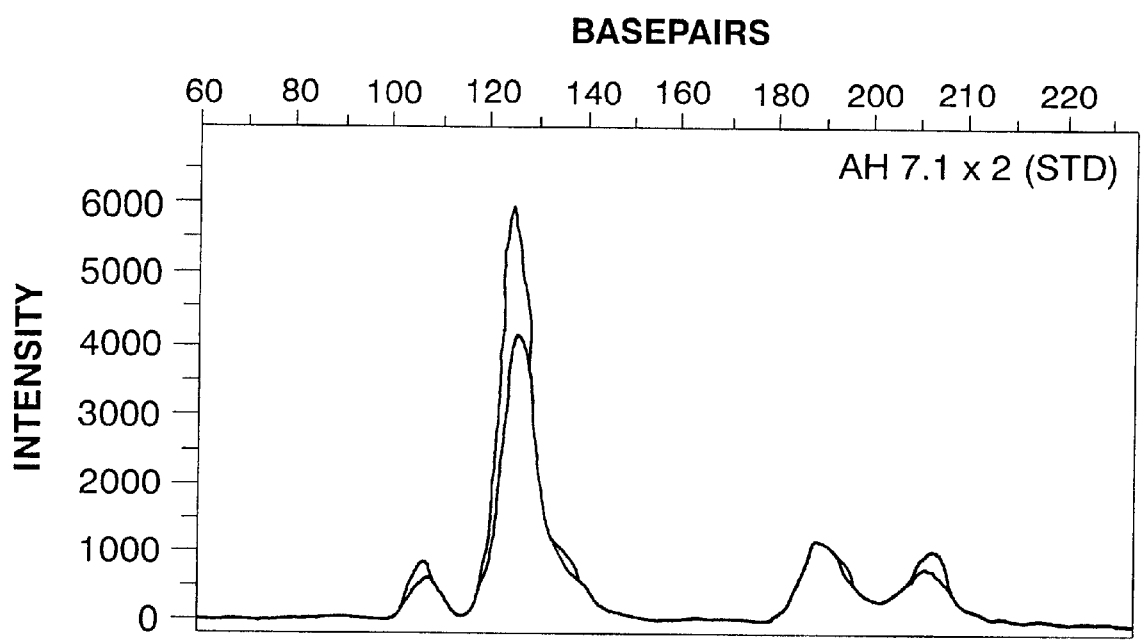
Figure 10F:
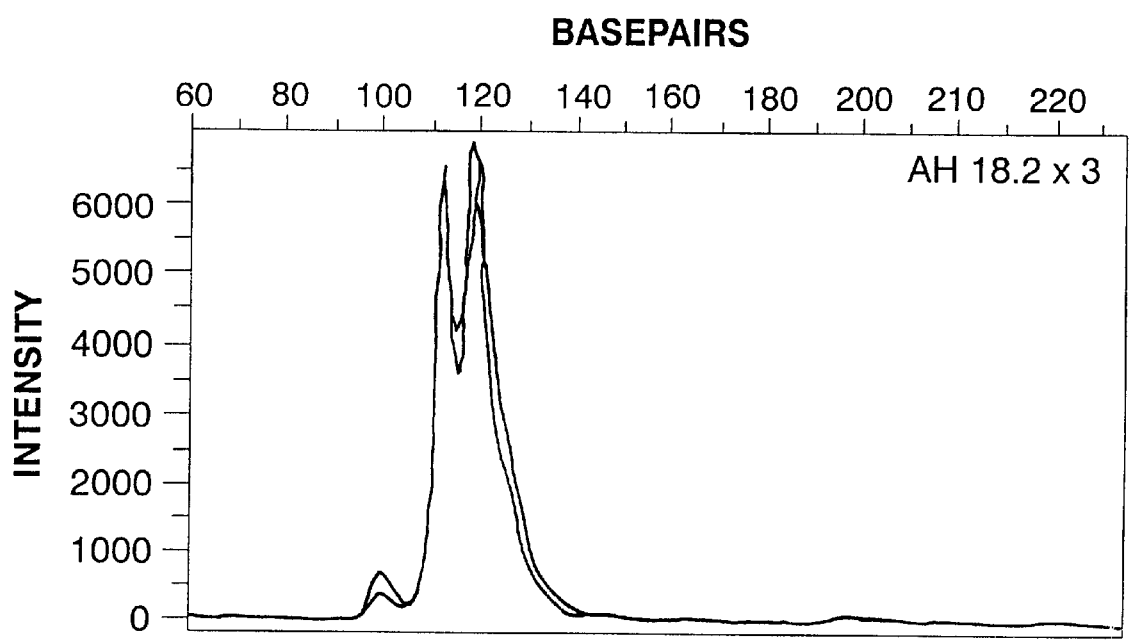
Figure 10G:
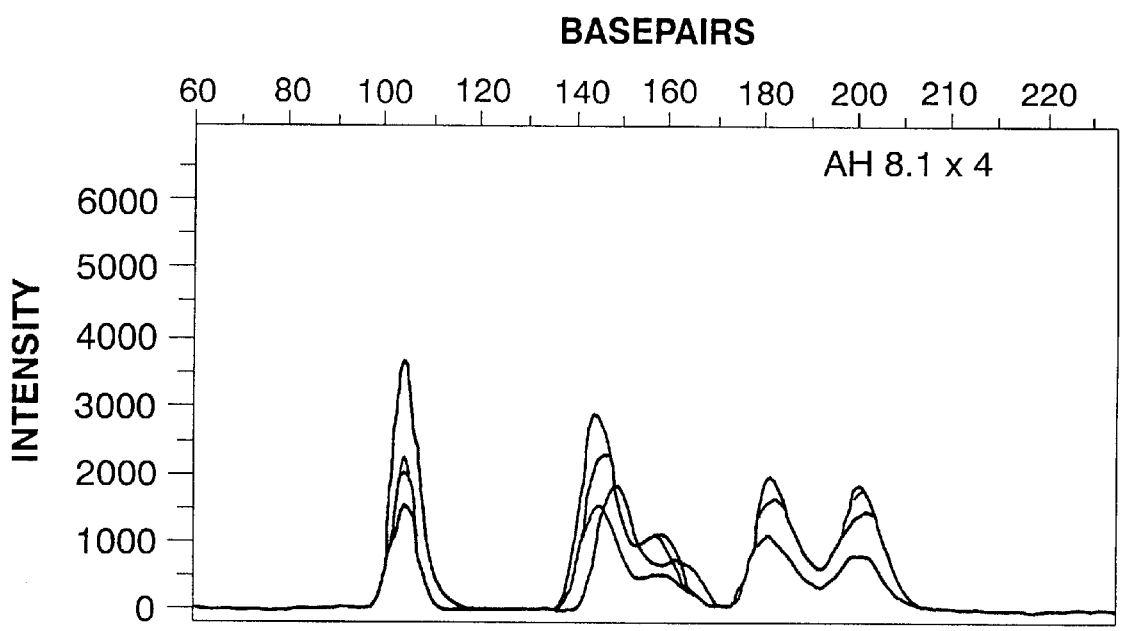
Figure 10H:
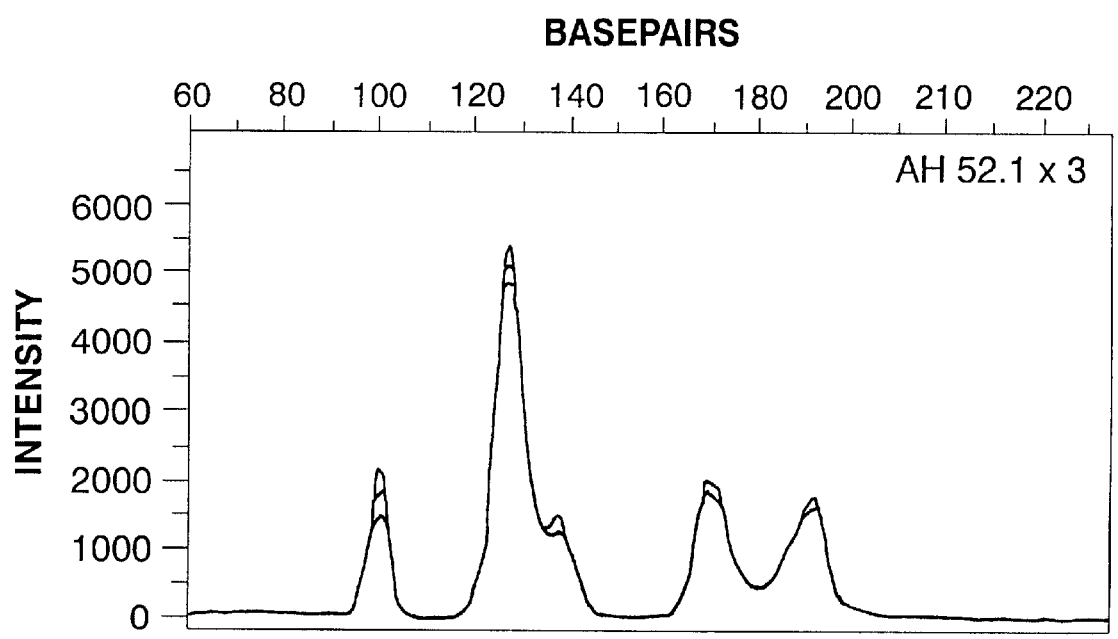

FIG. 7 profiles genotypically identical siblings and their parents. Siblings sharing the same nuclear ancestral haplorypes (a and c) give very similar profiles allowing for some variation in the total DNA concentration following PCR amplification (Panel 1). The profiles have the same number of fragments of the same size. Each parent (ab-father: Panel 2) and (cd-mother: Panel 3) can be distinguished from their off-spring indicating that it is possible to distinguish subjects who differ by only one ancestral haplotype. For instance in panel 2, the b ancestral haplotype contributes to the fragments at approxdmately 154 bp and 211 bp, and the increment in intensity of fragment at approximately 195 bp. It is also evident that the a and b ancestral haplotype does not contribute to the peak at approximately 128 bp. As shown in the third panel, ancestral haplotype d differs substantially from b in that its major contribution is to the peaks at approximately 128 and 215 bp.

FIG. 8 shows CL typing of donor/recipient pairs matching for bone marrow transplantation. The donors and recipients in panel a and b were serologically identical at HLA-A, B and identical at DRB1 by SSO typing. CL patterns of donor and recipient differed in both cases. Interestingly, in both cases the engraftment failed at 14 days. Similar CL typing patterns in donors and recipients in panels c and dwere associated with successful graft outcomes.

FIG. 9 shows the results following the selection of four cell lines on the basis that they were homozygous for the 8.1 ancestral haplotype by other MHC typing. Superimposition of the profiles indicates that the four are at least very similar. Some minor differences are at least partially explicable in terms of differing relative DNA concentrations following amplification.

FIGS. 10 (10a and 10b) shows CL analysis of homozygous cell lines indicate that different patterns are obtained when comparing seven different ancestral haplotypes. In fact each of these profiles has been seen with at least one other example of the same ancestral haplotppe suggesting that the patterns are reproducible. Although the profiles of 7.1, 46.1 and 62.1 appear to be very similar, small differences in peak positions are evident (refer to Table 4).

Figure 11A:
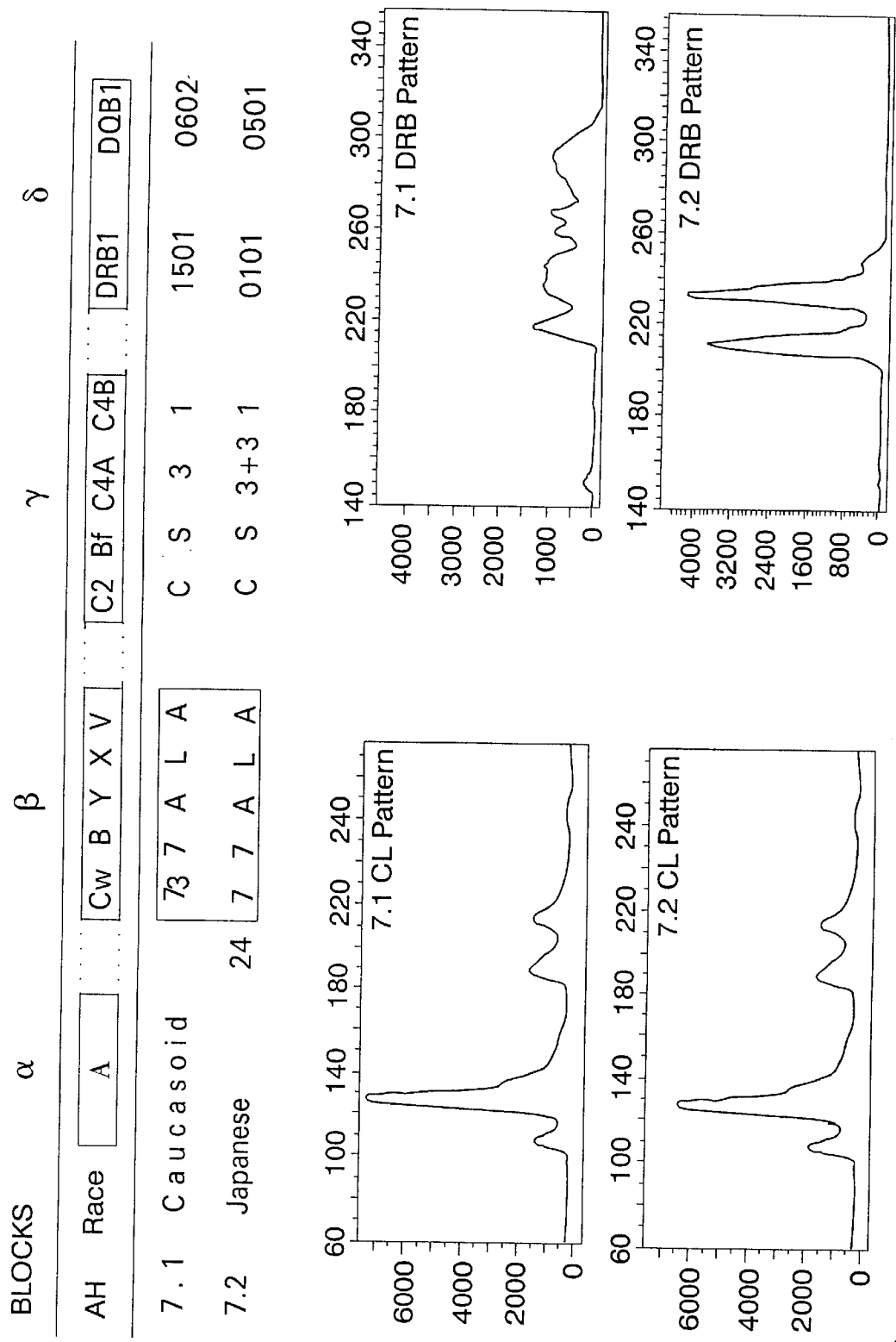
Figure 11B:
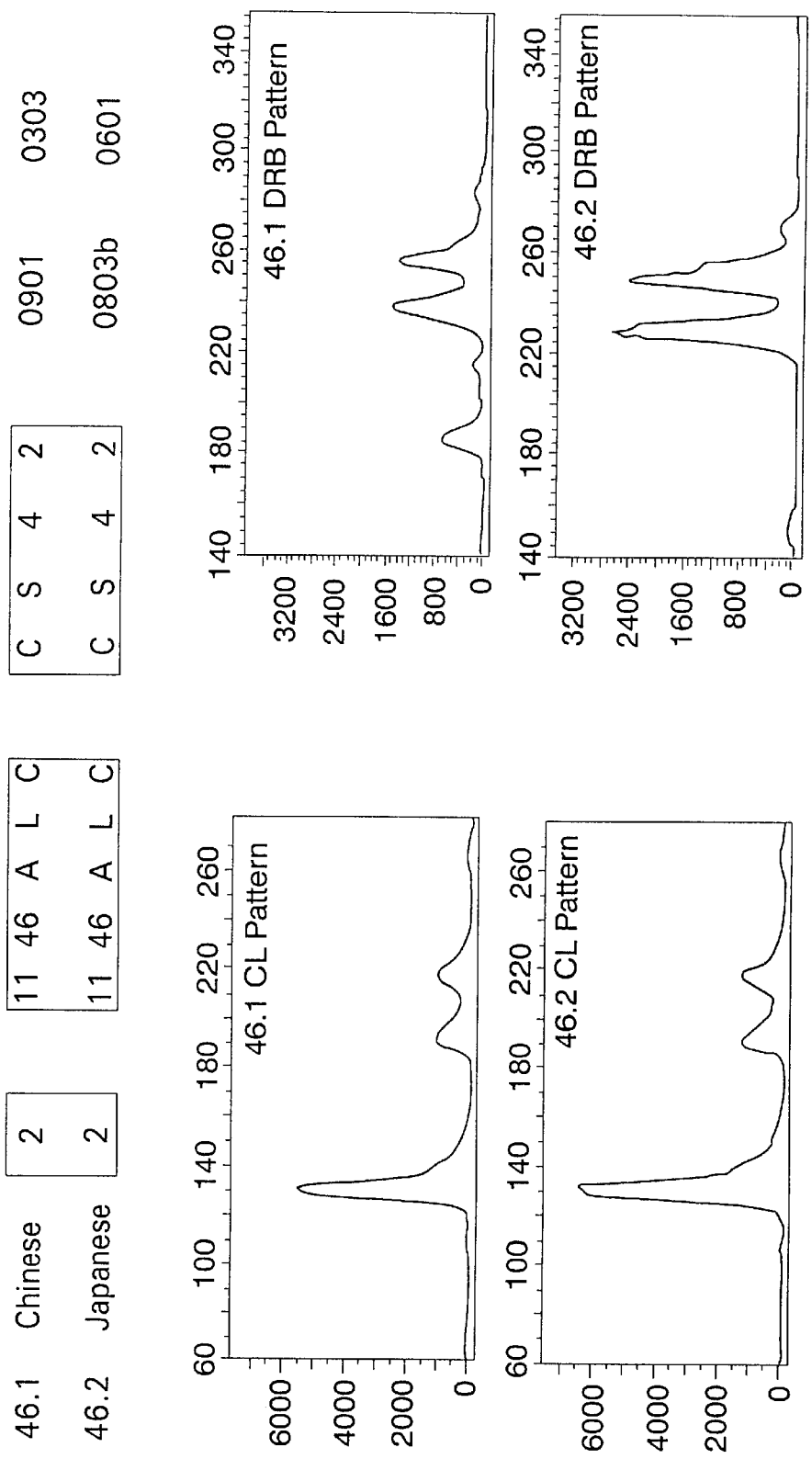

FIG. 11 (11a and 11b) shows that CL and DRB patterns reveal similarities and differences between related ancestral haplotypes. As shown, the same beta blocks (shaded) are shared between 7.1 and 7.2 and between 46.1 and 46.2 using markers defined at serological and DNA levels. As expected, CL typing patterns show identity when 7.1 is compared with 7.2 and between 46.1 and 46.2. The differences in delta blocks of the two groups can be demonstrated when DRB patterns within both groups are compared.

DRB typing was performed using the same reaction composition with DRB specific primers and the same PCR regime as for CL typing. The primers specific for DRB typing were designed from published sequences[24]. 50 pmol of each FAM (Applied Biosystems Inc. Foster City, Calif.) labelled DRB2.a61 (5'X-TGG AAC AGC CAG AAG GAC 3') and ODRBrep (5'GAT AGA GAG GAT TCT AAA TG 3')[24] were used. As for CL typing, the PCR products were resolved on 3% Seaplaque (1×TBE) (FMC Corp, Rockland, Mass.) by electrophoresis (100 volts over 8 hrs) in the ABI 362-Genescanner.

Figure 12A:
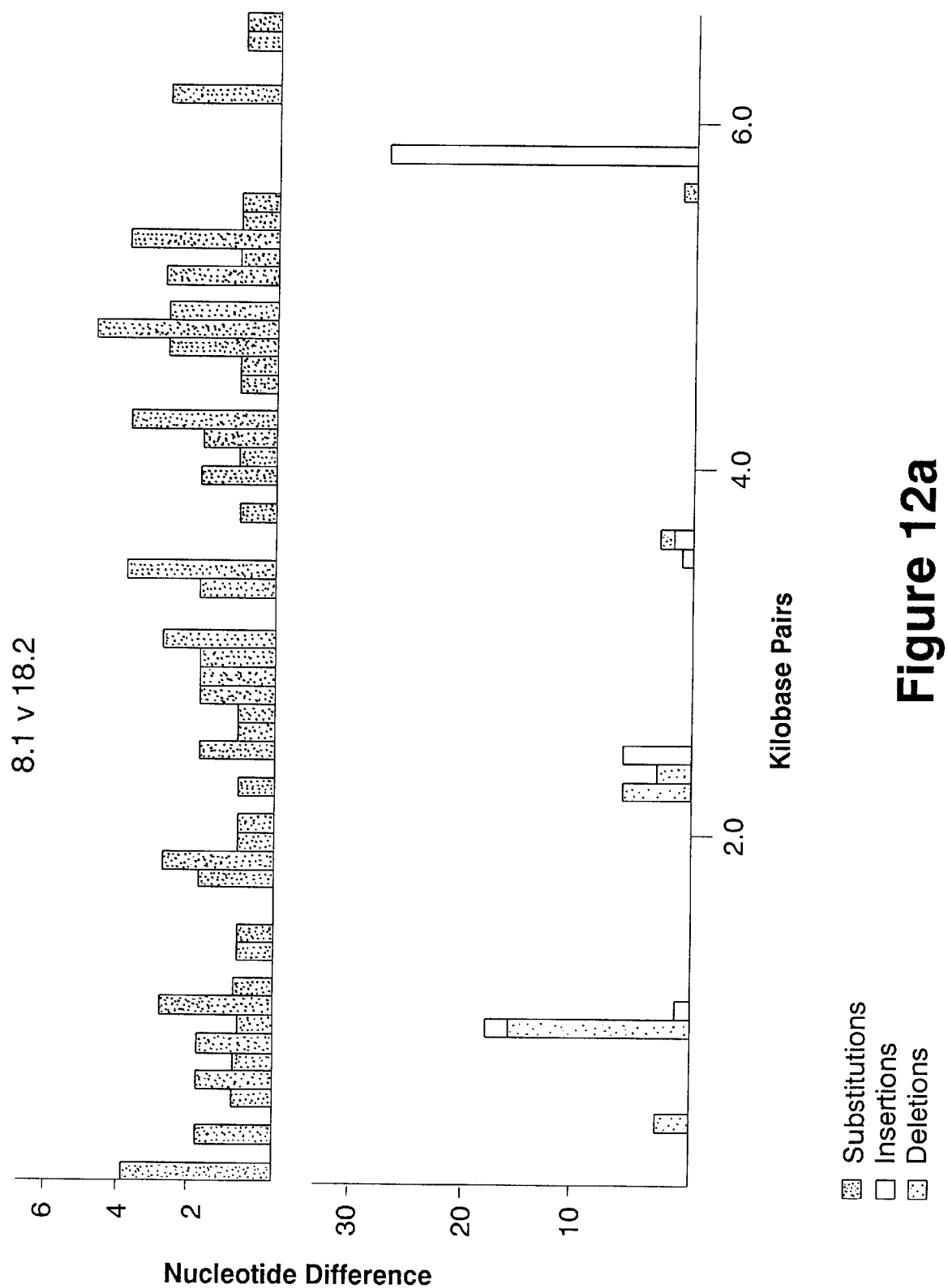
Figure 12B:
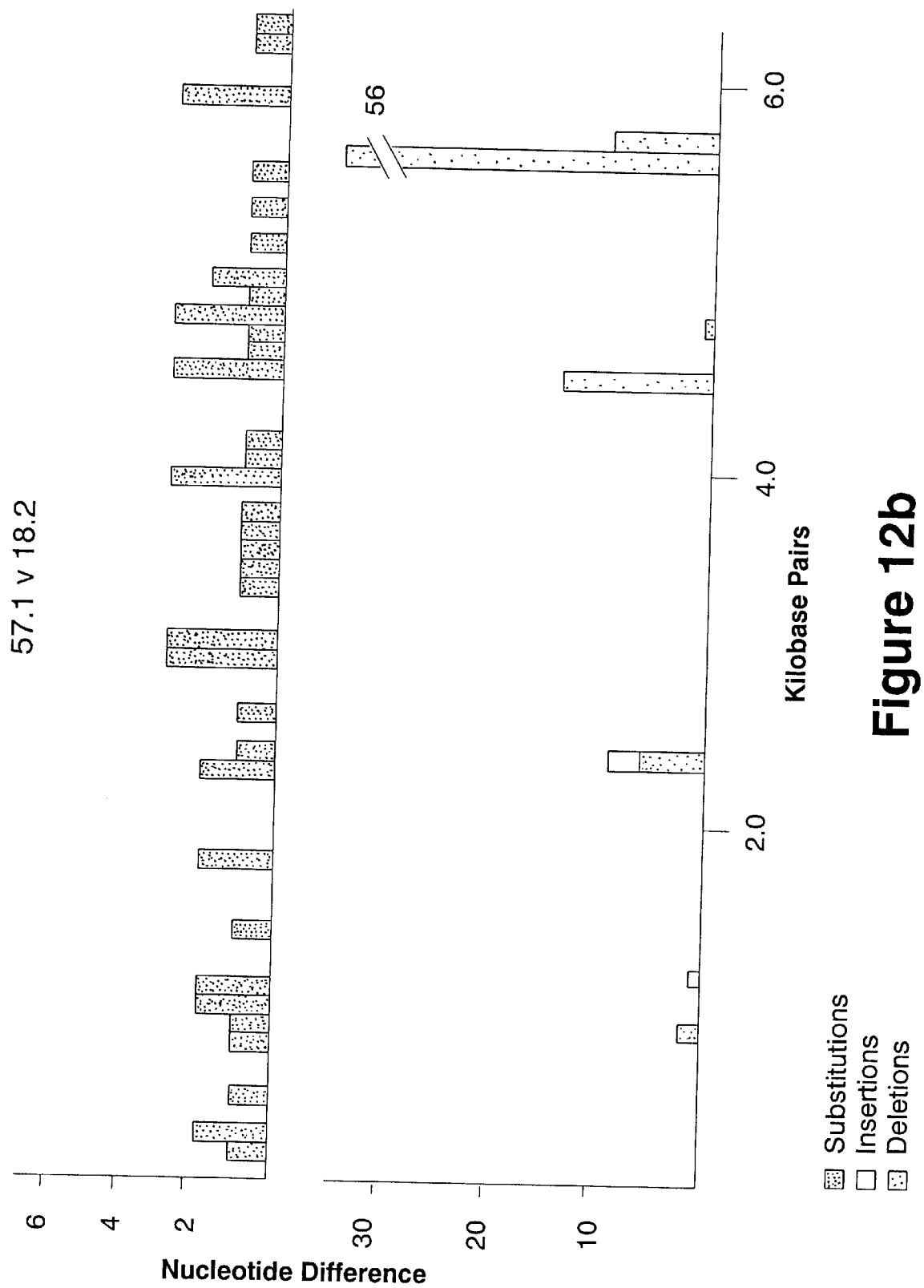
Figure 12C:
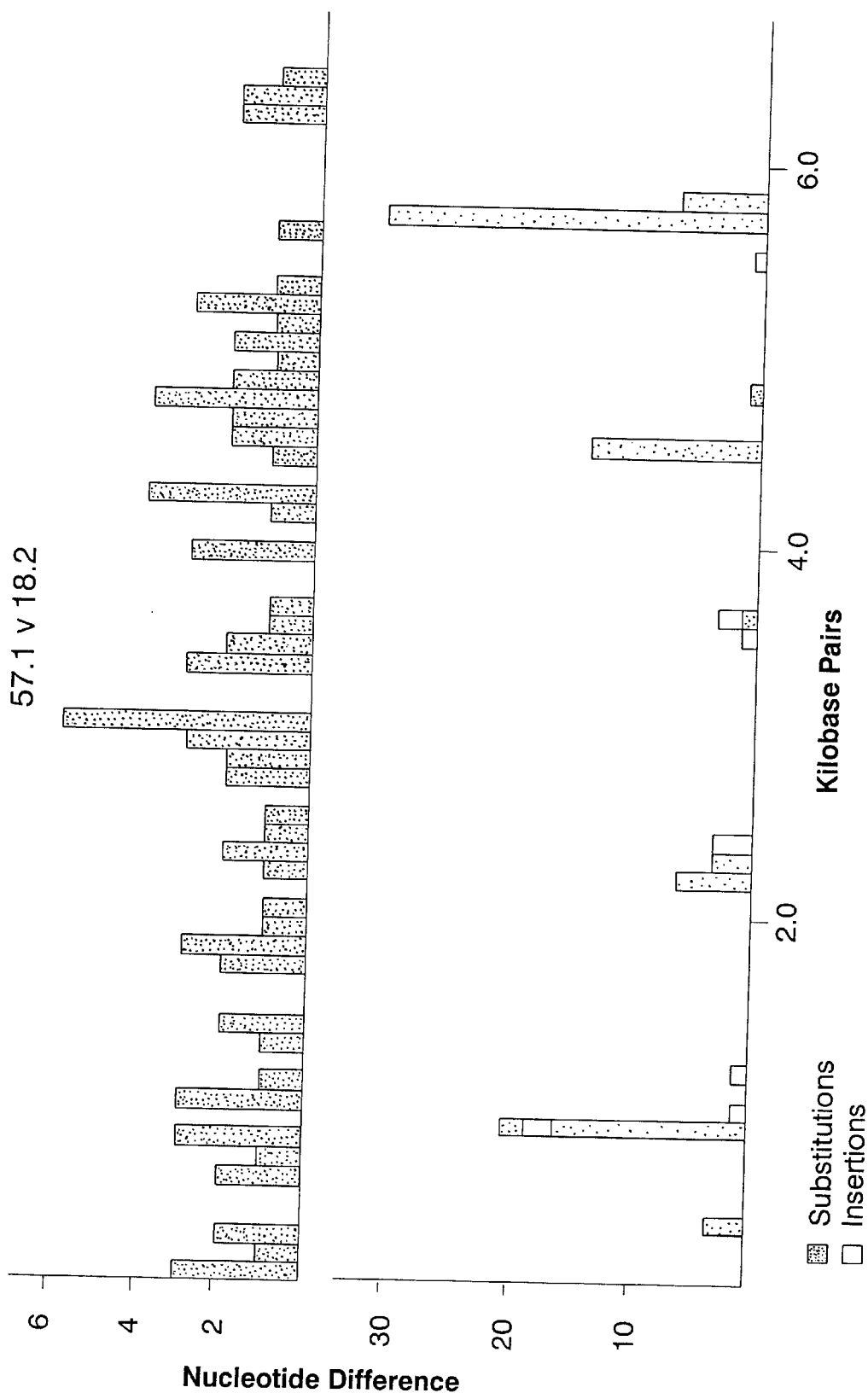

FIG. 12 is a comparative sequence analysis of 6.4 kb of CL1 from ancestral haplotypes 8.1, 18.2 and 57.1. (The CL1 sequence has been deposited in Genbank, accession number L04965). Pairwise histograms illustrate the number of nucleotide substitutions per 50 bp interval (upper panels) and number of inserted or deleted nucleotides per 100 bp interval (lower panels) between 8.1 and 18.2, 57.1 and 18.2 and 57.1 and 8.1.

Figure 13:
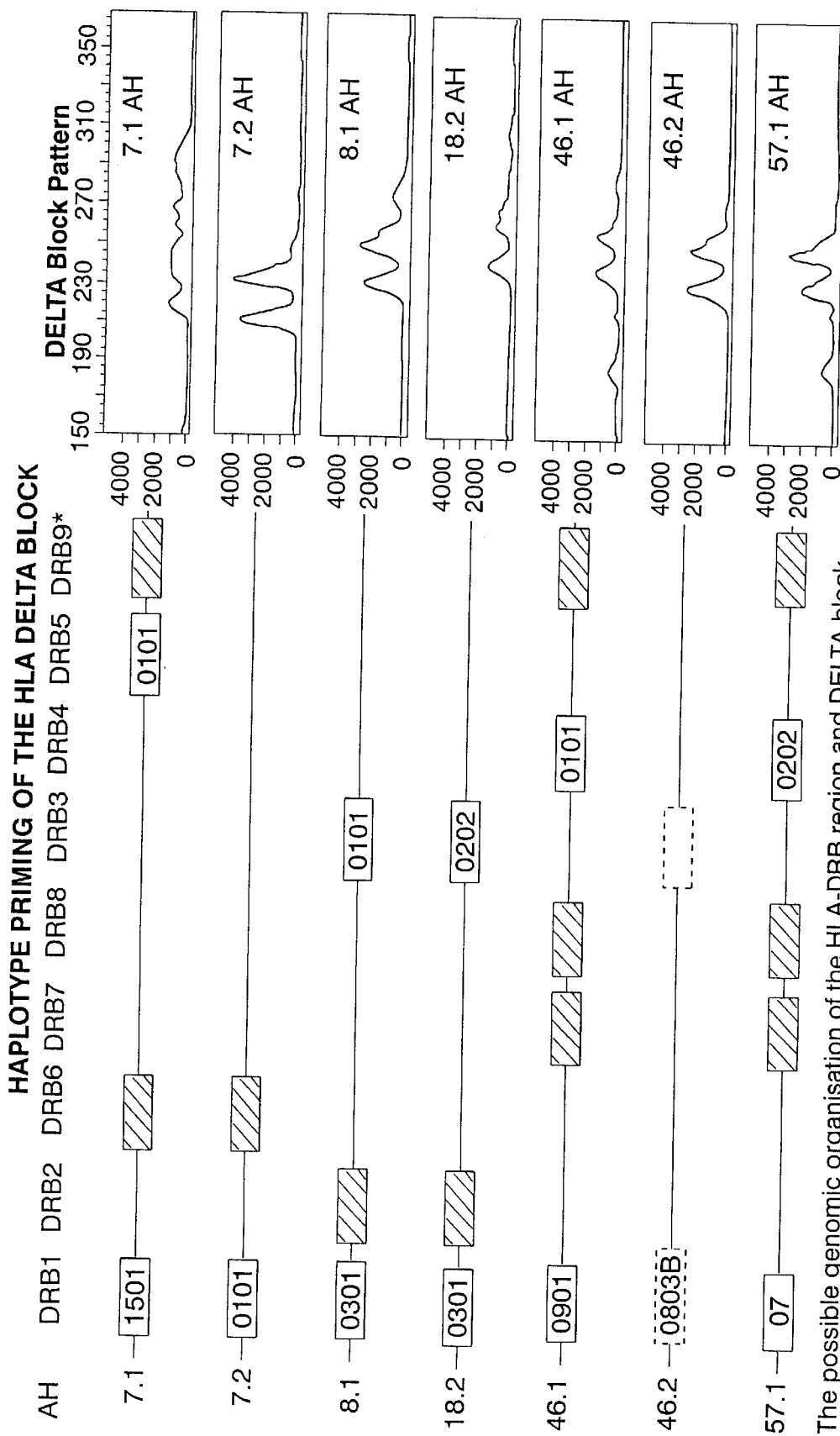

FIG. 13 is a diagramatic representation of haplotype priming of the HLA delta block.

EXAMPLE 1

Production of Cell Lines Homozygous for Ancestral Haplotypes of the Human Major Histocompatibility Complex:

B lymphocytes were transformed with Epstein Barr Virus (EBV) using whole blood frozen in dimethyl sulphoxide.

Materials:
1. RPMI 1640 medium (GIBCO)
2. Foetal calf serum (FCS)
3. Penicillin gentamycin sulphate (PGS)—use 200 units/ml and 10 μg/ml final concentration
4. EBV—prepared from B95-8 cell line
5. NUNC (Trademark) tubes
6. Costar tissue culture flasks 3055 (50 ml)
7. Dimethyl sulphoxide (DMSO) Analar Method:

A. Specimen Collection:
1. Collect 10 mls blood into sodium citrate or heparinised anticoagulant tubes. Spin 500 G/10 mins. Collect 1.5 ml buffy coat. Prepare four 0.25 ml aliquotes of buffy coat in NUNC tubes and place at 4° C. for 30 minutes.
2. Add 0.025 mls DMSO (10% V/V) to each 0.25 ml aliquot of buffy coat NUNC tube.
3. Place NUNCs at −70° C. to −80 ° C. in plastic rack or cardboard box for a minimum of two hours. Store in liquid nitrogen.

Buffy coat gives best results but whole blood may be used. Use the above protocol except add 0.05 ml of DMSO to 0.5 ml aliquot of whole blood.

B. Transformation:
1. Next day or subsequently, rapidly thaw one 0.25 ml aliquot in a 37–41° C. waterbath.
2. Resuspend in 10 ml RPMI and then centrifuge for 2 minutes at 2500 rpm.
3. Resuspend to 0.5 ml with 10% FCS in RPMI PGS (growth medium)
4. Infect with 0.1–1.0 ml of EBV supernatant and add 2.5 ml of growth medium.
5. Add 1 ml growth medium after 3–4 days.
6. Transfer to 50 ml culture flask 5–7 days later.

Method for Making, Freezing and Thawing EBV Cell Lines:

Viable cells are frozen slowly 1–2 ° C. drop/minute keeping ice crystal formation to a minimum. Rapid thawing in warm water optimises recovery of viable cells.

Reagents:
20% Foetal calf serum (FCS) in RPMI 1640
15% Dimethyl sulphoxide (DMSO) in RPMI 1640
Beckman tubes or Nunc tubes
Sterile Method: (aseptic)
1. Resuspend cells to be frozen in RPMI containing 20% foetal calf serum at a concentration of $10 \times 10^6$/ml.
2. Cool cell suspension in a melting ice bath.
3. Add an equal volume of precooled 15% DMSO in RPMI dropwise, to the cooled cell suspension. Ensure there is adequate mixing while adding DMSO. An alternative is to add a freezing cocktail (10% DMSO 15% FCS, 75% RPMI 1640) directly to the cell pellet.
4. Fill tubes with cells in freezing cocktail and keep at 4° C. until all tubes are filled.
5. Transfer tubes to a −70° C. freezer to facilitate freezing at 1–2° C. drop/minute.
6. Transfer tubes to liquid nitrogen within two days.

Family studies were conducted by HLA typing on immortalised lymphocytes produced according to the above methods. HLA typing was carried out according to conventional procedures (Terasaki et al., 1976) and all members of a family were generally typed. Individuals typing as homozygous for a particular ancestral haplotype or heterozygous to two ancestral haplotypes or recombinants thereof were selected for further analysis.

A first patient designated R85 1518 was typed as follows:
Ancestral haplotypes:

| A | C | B | C4A | C4B | BF | DR | DQ |
|---|---|---|-----|-----|----|----|----|
| 1 | — | 8 | Qo | 1 | S | 3 | — |
| 9 | — | 8 | Qo | 1 | s | 3 | — |

This individual typed as ancestral haplotype 8.1 and was homozygous for this ancestral haplotype.

A second individual, designated R85 5054 was typed as follows:

| A | C | B | C4A | C4B | BF | DR | DQ |
|---|---|---|-----|-----|----|----|----|
| 2 | — | 18 | 3 | Qo | F1 | 3 | 3 |
| 19 | — | 18 | 3 | Qo | F1 | 3 | 3 |

This individual typed as ancestral haplotype 18.2 and was shown to be homozygous for this ancestral haplotype by the above serotypic analysis.

Human cell lines homozygous to the following human ancestral haplotypes were produced according to the aforementioned methods:

7.1, 7.2, 18.1, 13.1, 18.1, 18.2, 35.1, 42.1, 44.1, 45.2, 44.3, 46.1, 46.2, 47.1, 52.1, 54.1, 57.1, 60.3, 62.1, 62.2 and 65.1.

EXAMPLE 2

Construcnon of Genomic Libraries from Haplospecific Cell Lines

Analysis of Genomic Clones:

A polynucleotide probe capable of hybridising to the Human Major Histocompatibility Complex, hereinafter referred to as Y, was derived from clone M20A (Spies et al. 1989). The location of this probe is approximately 36 kb centomeric to HLA B. This probe was labelled with $\alpha$-[$^{32}$P]-dCTP by random priming (Sambrook et al., 1989). Lambda genomic clones of the region were isolated from 4 ancestral haplotypes; 8.1, 18.2, 57.1 and 7.1. Restriction analysis of 8.1, 57.1 and 7.1 clones with Bam Hi showed that 2 populations of overlapping clones were present. The two cloned regions, designated CL1 and CL2, were identified as carrying a hybridisable 6.5 kb or 4.5 kb Bam HI fragment, respectively. The results were confirmed by Southern hybridization analysis of genomic DNA. After digestion with Bam HI, two fragments (6 kb and 4.5 kb) of equal intensity were observed in ancestral haplotypes 8.1, 57.1, 7.1 and 18.2. Southern analysis confirmed that the hybridizing regions were duplicated in all 4 ancestral haplotypes and marked by two BAM HI fragments of 6.5 kb and 4.5 kb. Pulsed field gel electrophoresis (PFGE) showed that the 6.5 and 4.5 kb fragments are within approximately 30 kb of each other in the MHC interval between TNF and HLA B. The 6.5 kb and 4.5 kb Bam HI fragments from the 4 ancestral haplotypes (except 18.2–4.5 kb Bam HI) were subcloned into either pGEMTZf(+) or pBCKS(+) and sequenced after preparation of Exonuclease III generated deletion clones or primer walking (Sambrook, et al., 1989). Sequence analysis was carried out using fluorescent dye-labelled M13 primers and a cycle sequencing kit (Applied Biosystems Inc.). Fluorescent dye labelled extension products were analysed on a Model 373 DNA Sequencer (Applied Biosystems Inc.). Sequence data editing and alignments were done using the Seq. Ed program (ABI) on a Macintosh Cl (Apple Computer Inc., Cupertino, Calif.).

Figure 1C:
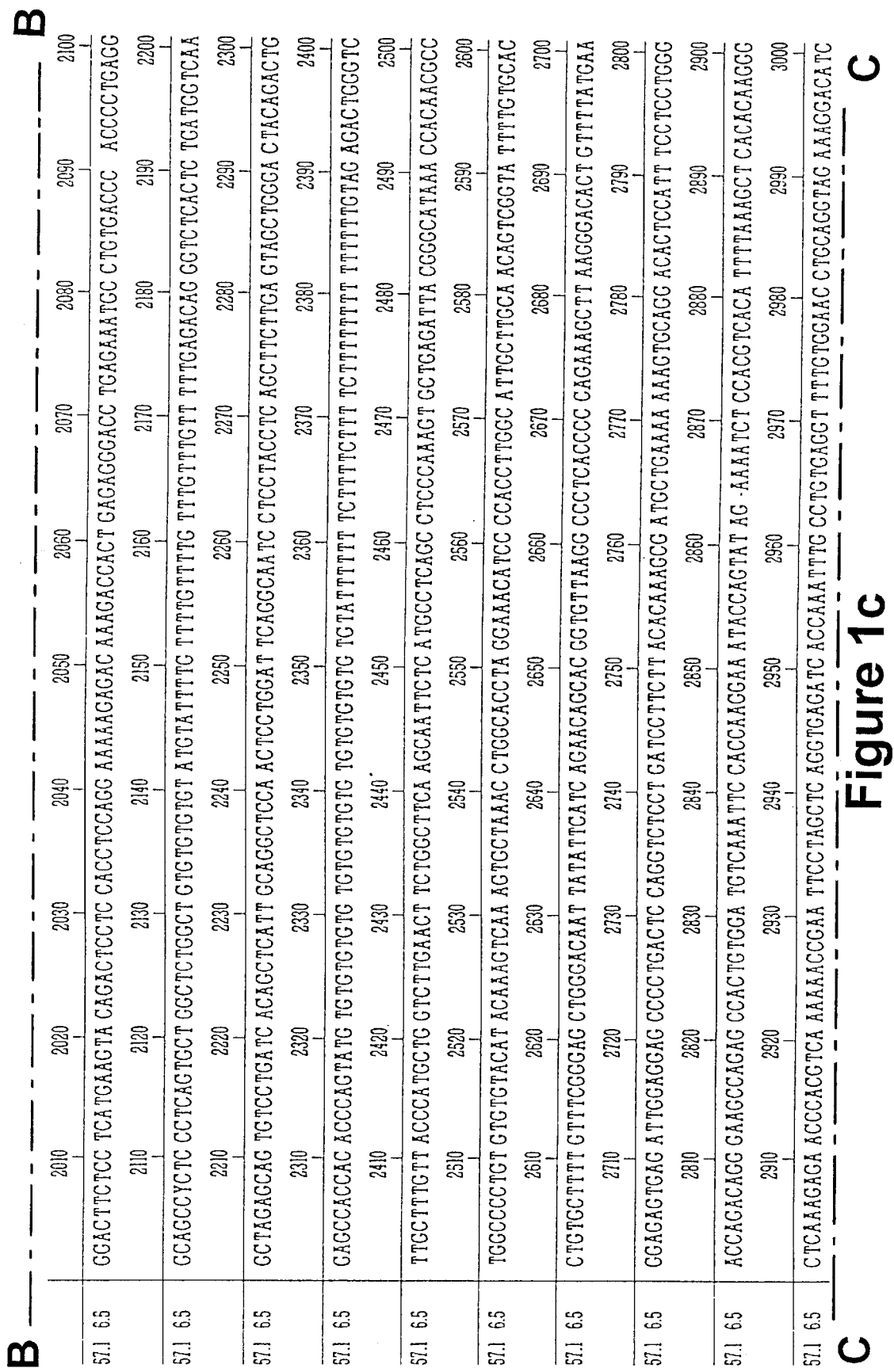
Figure 1D:
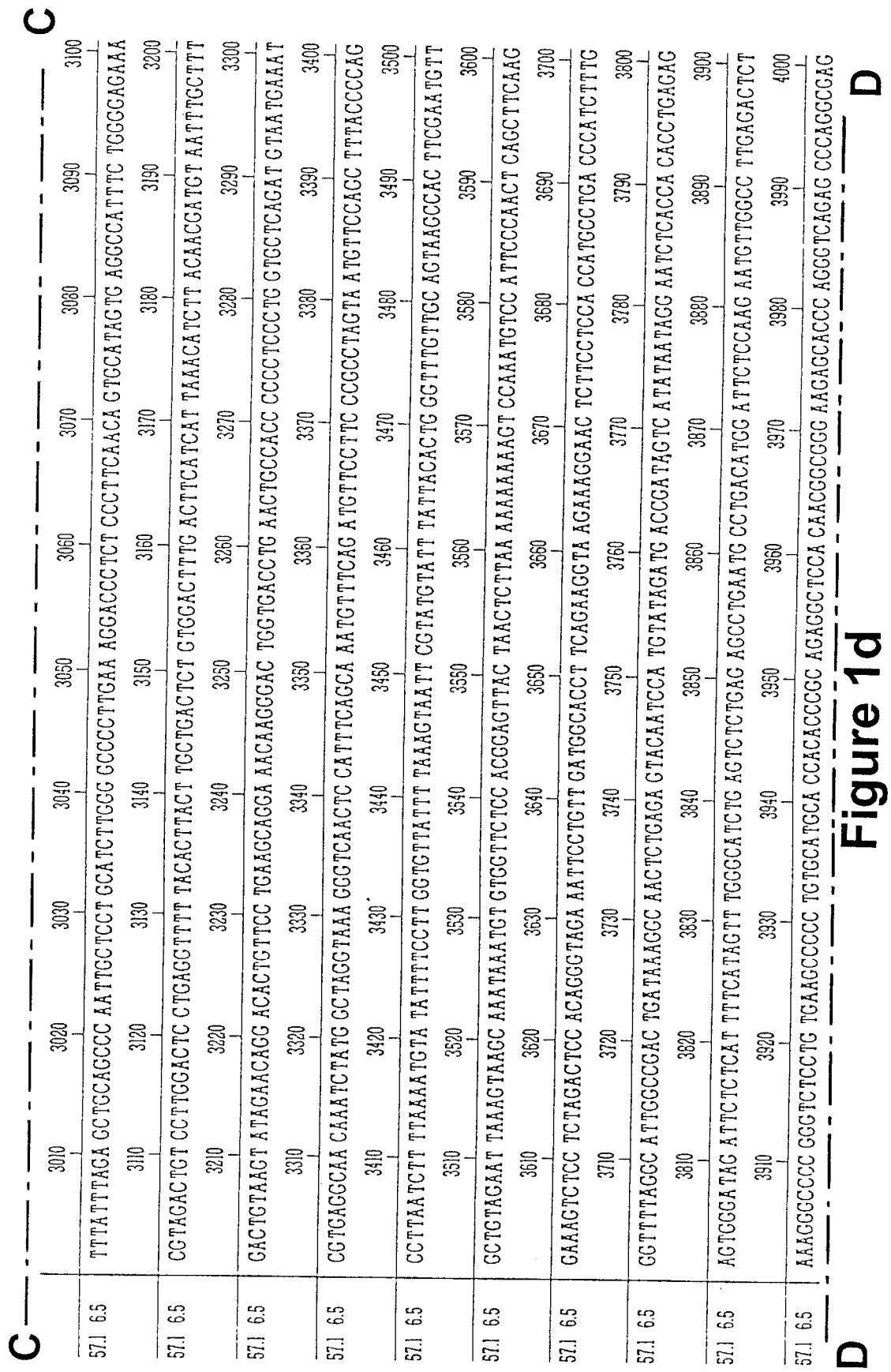

The sequence analysis of the 57.1 6.5 kb Bam Hi fragment is shown in FIG. 1. Sequence analysis of the other ancestral haplotypes was determined but is not shown. From a comparison of the nucleotide sequences of the 6.5 and 4.5 kb Bam HI fragments of the various ancestral haplotypes, regions of extreme localised polymorphism between ancestral haplotypes were recognised and designated HGEs.

In Table 1, nucleotide sequences of Haplotype Specific Geometric Elements (HGE) for respective ancestral haplotypes are given. As will be readily apparent, the sequence contains (but is not necessarily restricted to) reiterated dinucleotides and possibly other non-random patterns. There is also some apparent symmetry around the region which is deleted or inserted (Table 1). Nucleotide sequences flanking the various HGEs are conserved for at least 100 base pairs. This is an important finding as probes produced from these conserved regions can be used to detect/characterise HGEs characteristic of a particular ancestral haplotype of the human Major Histocompatibility Complex.

The data of Table 1 is presented in a different manner in Table 2 (Note: shaded regions in Table 2 represent "T G T G T G T G T G T G" and "T G T C T G" respectively.

From Table 2 it is evident that the HGE sequences show insertional/deletional variation between each ancestral haplotype. Such variations are the most efficient way to generate polymorphism.

It is to be appreciated that the following methods for detecting ancestral haplotype using Haplospecific Geometric Elements focuses on variations within non-conserved regions, this correlating with deletions/insertions which alter the length or number of nucleotides within a Haplospecific Geometric Element.

While Haplospecific Geometric Elements of the human MHC appear to be the principle focus for variation, as largely represented by nucleotide deletions, and to some extent insertions, variations between ancestral haplotypes occur along the rest of the ancestral haplotype sequence (as represented by nucleotide deletions/insertions and nucleotide substitutions—FIG. 12). Therefore, sequence variation outside of Haplospecific Geometric Elements may also be utilised to distinguish between ancestral haplotypes.

It is important to note that the CL1 of each ancestral haplotype is a duplication of the CL2 region.

TABLE 2

The haplospecific geometric elements in the CL region show a degree of geometry and symmetry.

| | UNIT LENGTH | |
|---|---|---|
| | nucleotides | unit of 7 |
| 57.1-CL1   TCAGA[N]TCTCTCTCTCTCTCTCTCTCTC░░░░░░░░░░░░░░░░TCTCTCTCTCTCTCTCTCTCaTTT | 94 | 12 |
| 57.1-CL2   ...TA......[ 28 ].................[ 10 ].T............ | 58 | 8.3 |
| 18.2-CL1   ...[ 38 ].................[ 30 ].... | 28 | 4 |
| 8.1-CL1    ...[N]........[ 22 ].................[ 16 ].......... | 56 | 8 |
| 8.1-CL2    ...TC..............C.C...C.C.C.......G...............C.C.........G........ | 96 | 13.7 |
| 7.1-CL1    ...[ 38 ].................C[ 28 ].... | 30 | 4.3 |
| 7.1-CL2    ...[N]..............C.C...C.C.C.......G...............C.C.........G........ | 94 | 12 |

. = consensus sequences
[N] number of deleted nucleotides

EXAMPLE 3

Detection of Ancestral Haplotype Using Primer Specific Amplification

Oligonucleotide primers flanking the HGE sequences as set forth in Example 2 are synthesised according to standard methods (Applied Biosystems User Bulletin, Issue 13, Apr. 1 (1987)).

The PCR primers CTREP 3 and CTREP 4 (hereinafter described) delimit a HGE sequence located in the CL1 region. These were synthesised using phosphoramidite chemistryon a Model 391 DNA Synthesizer (Applied Biosystems Inc.) deprotected and purified. The primer sequences are set forth in Table 3.

TABLE 3

| Sequence Name | |
|---|---|
| CTREP 3 | T G T A A A A C G A C G G C C A G T ↑ A C A A G<br>C C C C C A G C A G A A T T C T G C T T |
| CTREP 4 | C A G G A A A C A G C T A T G A C C ↑ G A C T A<br>T C C A G A A G T C A C A G C T A C T C |

The first 18 nucleotides of the above primers represent M13 universal (CTREP 3) and M13 reverse (CTREP 4) sequencing primers. Accordingly the first 18 nucleotides may be removed from these sequences.

Amplification of HGE Sequences:

A panel of 29 EBV-transformed human B cell lines were analysed. These cells were obtained from EBV transformation of peripheral blood lymphocytes (PBLs) or from the 10th International Histocompatibility Workshop reference cell panel. The cell lines were genoryped for HLA class I, II and complement loci by serology, complement allotyping or RFLP analysis. Cell lines that were homozygous for a particular ancestral haplotype were selected for inclusion on the panel. DNA was isolated from 12 homozygous cell lines using a Proteinase K/phenol extraction procedure as described (Dawkins et al., *J. Immunogenetics* 14:89 (1987)).

PCR and Analysis of Products:

Polyrnerase chain reactions (PCR) were performed in a volume of 100 µl containing 500 ng of genomic DNA derived from individual EBV-transformed B-cell lines, 200 µM each of dATP, dCTP, dGTP and dTTP, 2.0 mM Tris-HCl (pH 8.3), 2.0 mM magnesium chloride, 50 mM KCl, 50 pmol each of CTREP 3 and CTREP 4 primers and 2 units of Taq DNA polymerase (Amplitaq, Cetus Corp.). Samples were overlaid with light mineral oil (Sigma) and subjected to thermocycling (30 cycles of 90° C. for 30 s., 55° C. for 30 s., 72° C. for 60 s.) followed by a final extension at 72° C. for 10 minutes. Products were analysed by electrophoresis in 3% Nusieve/1% Seakem agarose (FMC Corp., Rockland, Mass.), 1×TBE.

Figure 2:
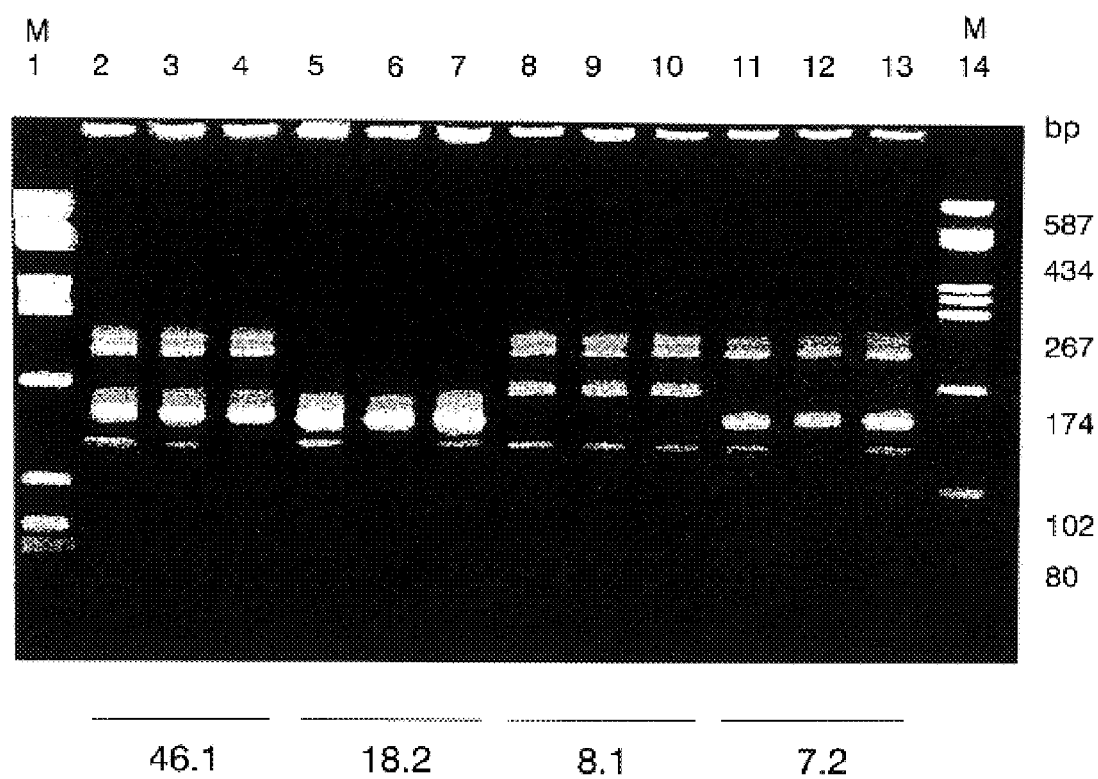
FIG. 2 shows DNA extracted from 12 homozygous cell lines representing three examples of ancestral haplotypes (AH): 46.1 (lanes 2–4), 18.2 (lanes 5–7), 8.1 (lanes 8–10) and 7.2 (lanes 11–13). Amplification using primers flanking the geometric elements demonstrates reproducible haplotypic patterns for all 4 ancestral haplotypes after electrophoresis in 3% Nusieve, 1% agarose gel. The molecular weight marker (M) in lanes 1 and 14 was pGEM-3 digested with Hae III.

The amplified products were separated by agarose gel electrophoresis and the resulting pattern is shown in FIG. 2 in respect of samples representing four ancestral haplotypes.

It is immediately apparent from FIG. 2 that each ancestral haplotype has a repeatable characteristic banding pattern with respect to both size and relative intensity. It is also apparent that primers could be produced to amplify various loci along the entire MHC ancestral haplotype from HLA A to HLA DQ.

As shown in FIG. 2, it is possible to amplify the CL1 and CL2 elements in genomic DNA from cell lines that are homozygous for ancestral haplotypes for which data of the CL region are not available and to obtain gel patterns which are characteristic to different ancestral haplotypes. In the 8.1 ancestral haplotype, for example, one would predict at least two bands of 173 base pairs and 213 base pairs that represent the addition of the primer lengths plus the distances between the primer sites in CL1 and CL2 respectively. The complex pattern seen in all cases may reflect the presence of additional hybridizing regions or interactions between specific PCR products. In any case, the patterns are typical for a particular ancestral haplotype and so must arise from the MHC loci.

Figure 3:
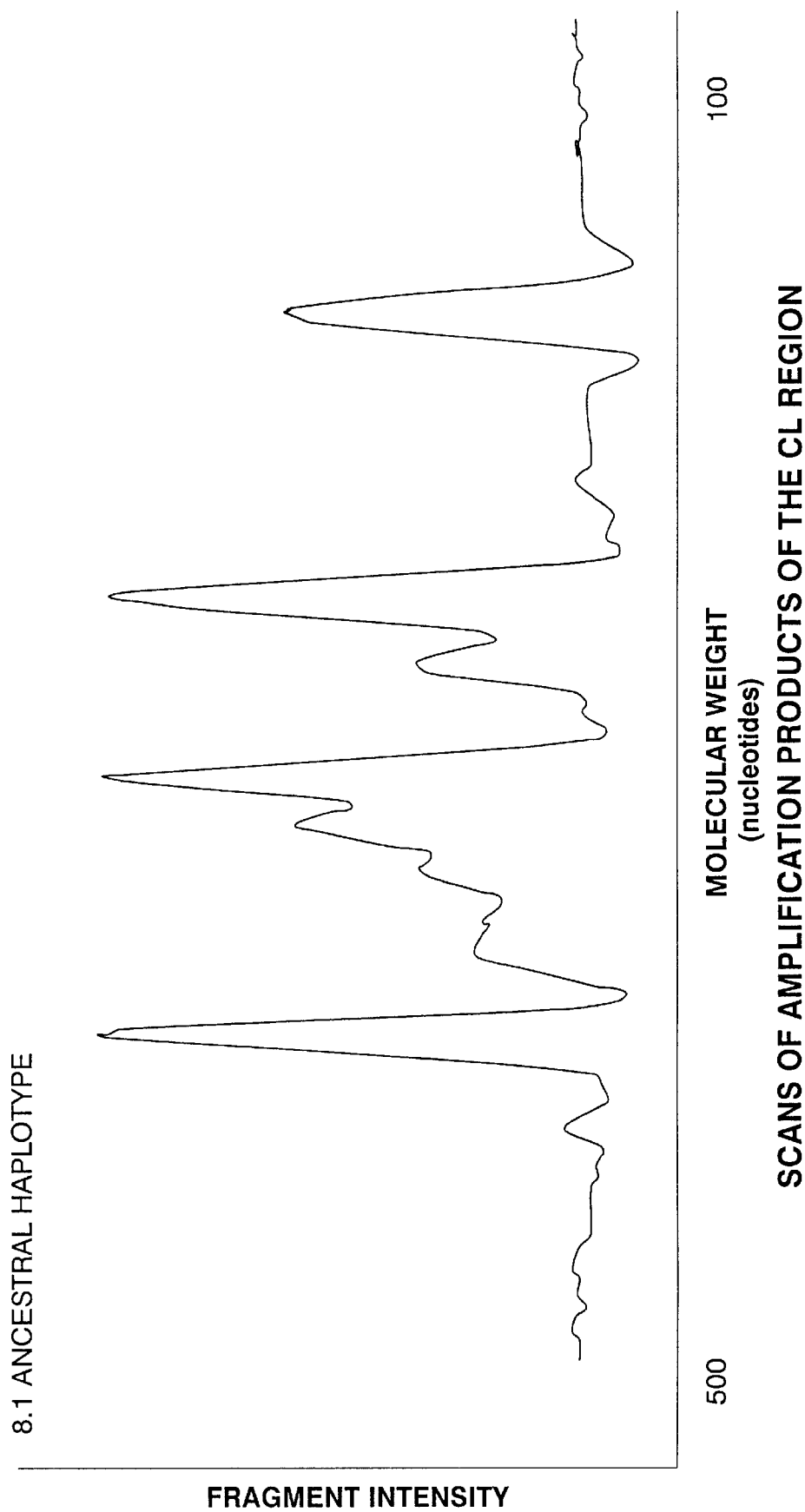
FIG. 3 shows a densitometry scan of the electrophoretic profile shown in FIG. 2 in respect of ancestral haplotype 8.1 (lanes 8 and 10). Fragment intensity is plotted against molecular weight (numbers of nucleotides) of scanned fragments.

FIG. 2 was scanned using a densimeter (Biorad) and the resulting scan for the 8.1 ancestral haplotype is shown in FIG. 3. This series of peaks is unique to the 8.1 ancestral haplotype. Each ancestral haplotype gives a particular scan which is readily distinguishable from other ancestral haplotype scans. Accordingly, a direct analysis of scanned amplified products allows a rapid identification of ancestral haplotype by comparison with reference scans of known ancestral haplotypes.

Figure 4A:
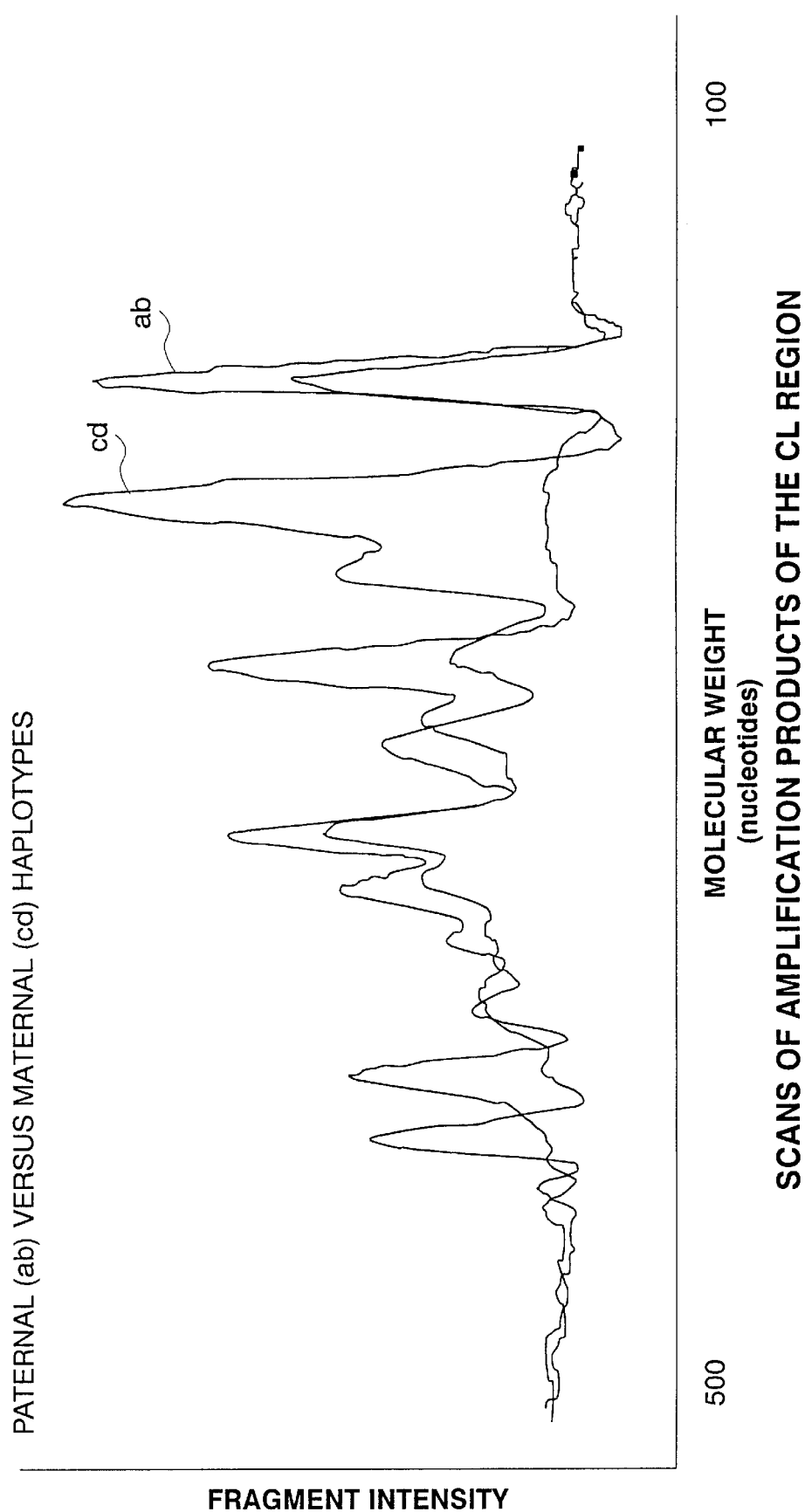
FIGS. 4A–4C shows a densitometry scan of DNA samples from a representative family (paternal 4A, maternal 4B, siblings 4C) amplified using primer CTREP 3 and CTREP 4, fractionated on an agarose gel and scanned with a densitometer (Biorad). Fragment intensity is plotted. against molecular weight (nucleotides). Paternal sequences are designated "ab", maternal sequences "cd" and sibling sequences "ac".
Figure 4B:
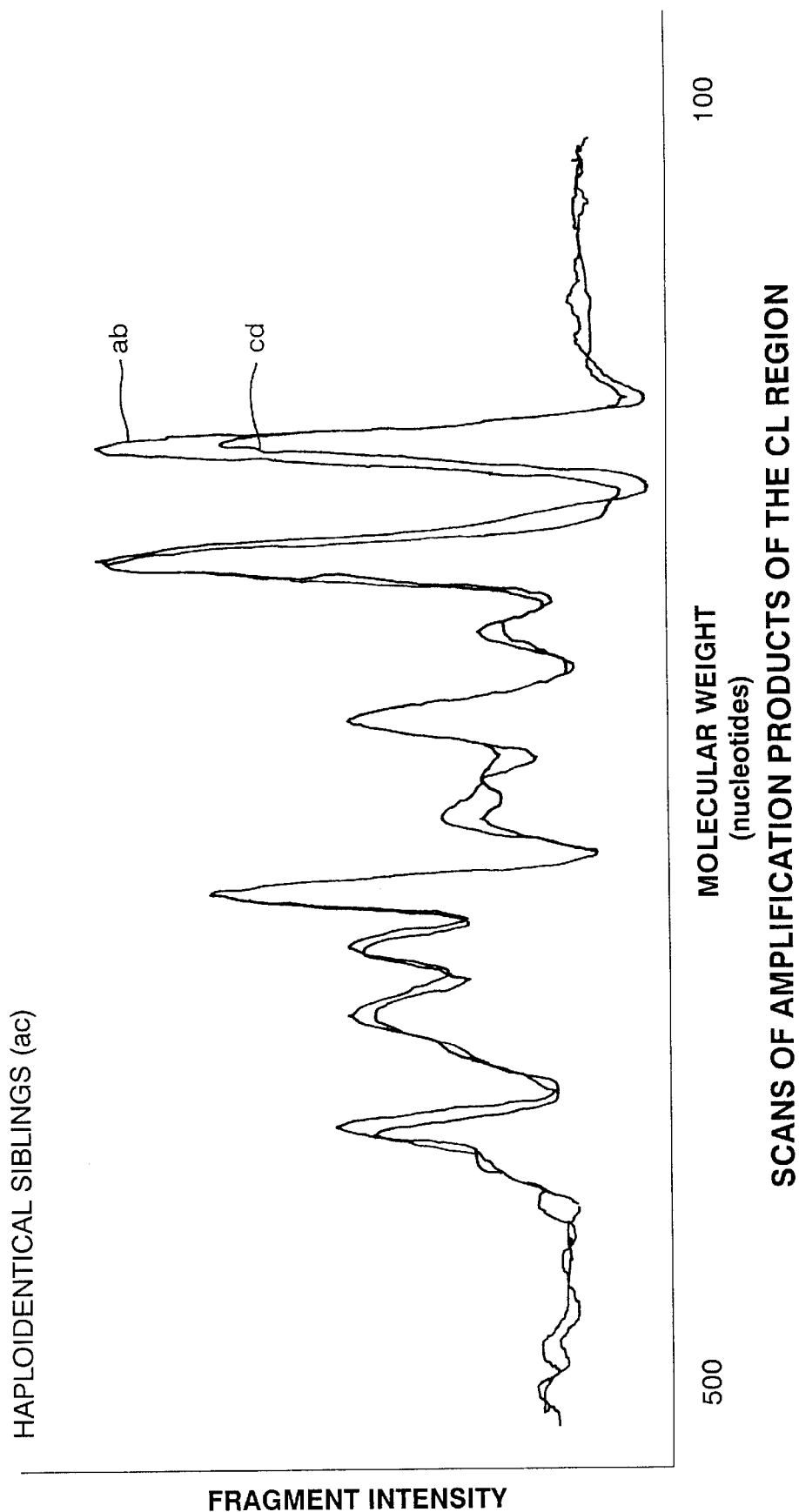
Figure 4C:
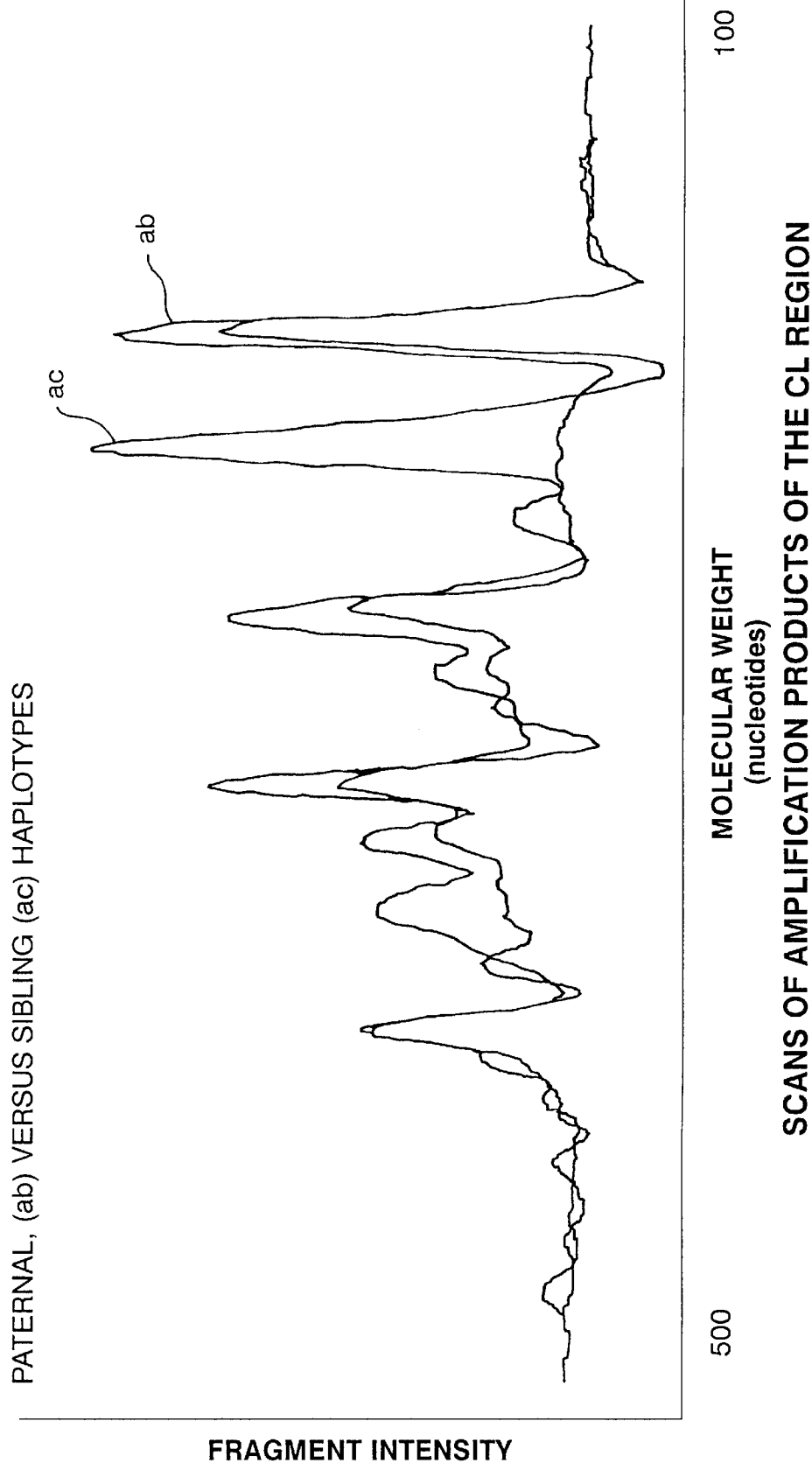

In a similar series of experiments, DNA samples were isolated from EBV transformed cell lines of a representative family. DNA amplification was conducted as above utilising primers CTREP 3 and CTREP 4, and the amplified fragments were fractionated on an agarose gel and scanned with a densitometer (Biorad). The densitometry scan is shown in FIGS. 4A to 4C which depict several comparisons between parents and siblings. As can be seen from FIG. 4A, paternal and maternal scans evidence HLA non-identity. While some fragments are shared, the scans clearly do not overlap. Siblings were haploidentical as shown in FIG. 4B where the traces overlap. Siblings possess the ac ancestral haplotypes, this being a combination of the paternal a ancestral haplotype and the maternal c ancestral haplotype. FIG. 4C shows a scan comparing paternal (ab) ancestral haplotype and sibling (ac) ancestral haplotype. This scan shows an intermediate picture where a number of peaks are coincident while others are clearly distinct.

The various scans of amplification products depicted in FIGS. 4A to 4C show that ancestral haplotype is assignable by comparison of ancestral haplotype sequences. Each ancestral haplotype gives a characteristic and unique scan, this scan reflecting variations in the length of the HGE sequence of each ancestral haplotype.

RFLP Analysis:

A DNA probe corresponding to sequences flanking CL1 and conserved between ancestral haplotypes (comprising nucleotides 1552 to 1823 of FIG. 1) was used in RFLP analysis of restricted DNA from 50 EBV transformed human cell lines. The cell panel covered 21 different ancestral haplotypes as set forth in Table 3.

Electrophoresis and Southern Blot Analysis:

Genomic DNA (10 µg) was digested to completion with Taq.I (Promega, Madison, USA) according to the manufacturer's instruction. In some blots double digestions of Taq I and Rsa I (Promega, Madison, USA) were used since additional fragments and improved patterns were obtained with the probe. The digests were electrophoresed on 1.1% agarose gels at 25 V for 62 hs (or on 0.8% agarose gels at 40 V for 18 hs) in 1×TBE buffer at room temperature (RT) and transferred to nylon membranes (GENESCREENPLUS, Du Pont, USA) by the method of Reed et al., using 0.4 M NaOH as a transfer medium. Prehybridisation and hybridisation of the membranes were performed in hybridization bottles (Hybaid Middlesex, U.K.) at 42° C. The membranes were washed twice with 2×SSPE for 10 min. at RT, once in 2×SSPE+0.5% SDS at 65° C. for 10 min and once in 0.5×SSPE at 65° C. for 5–10 min. Kodak X-OMAT films were exposed to the membranes at −70° C. for 1–10 days according to standard methods. The sizes of the restriction fragments were determined by reference to a 1 kb DNA ladder (BRL, Gaithersberg, U.S.A.). Probes were stripped off the membranes by treatment with 0.4 M NaOH. Stripping was carefully checked by exposure to fresh films and the membranes were then used for reprobing.

Figure 5:
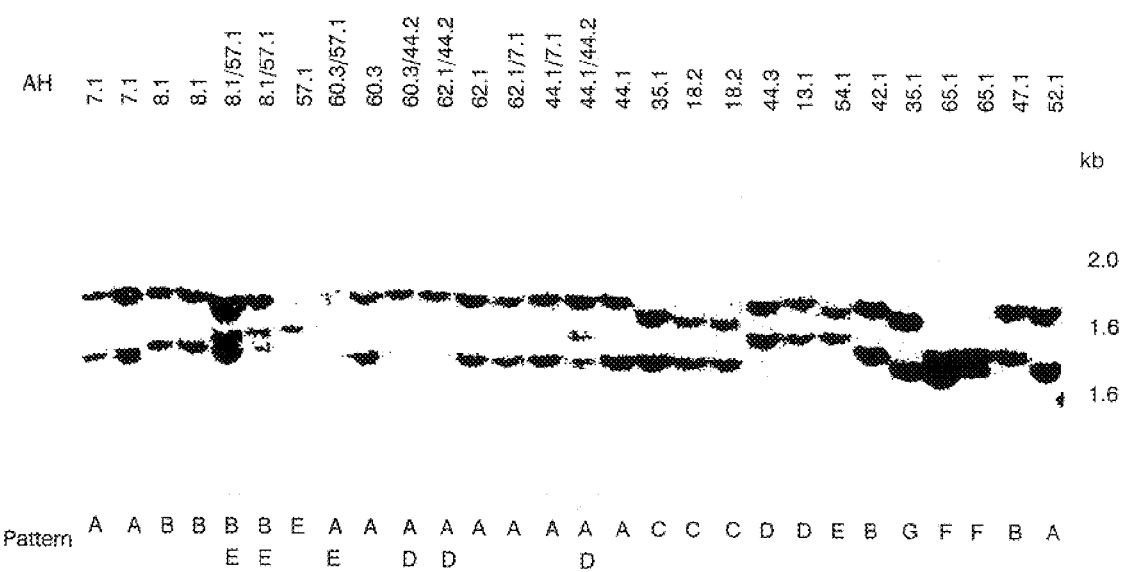
FIG. 5 shows double digestion of DNA isolated from cell lines homozygous for ancestral haplotypes using restriction endonucleases Taq I and Rsa I. The digests were fractionated on agarose gel electrophoresis and transferred onto nylon membranes and hybridised with a $^{32}p$ labelled fragment corresponding to nucleotides 1552 to 1823 of FIG. 1. Autoradiography was then conducted at −70° C. for 1 day.
Figure 6A:
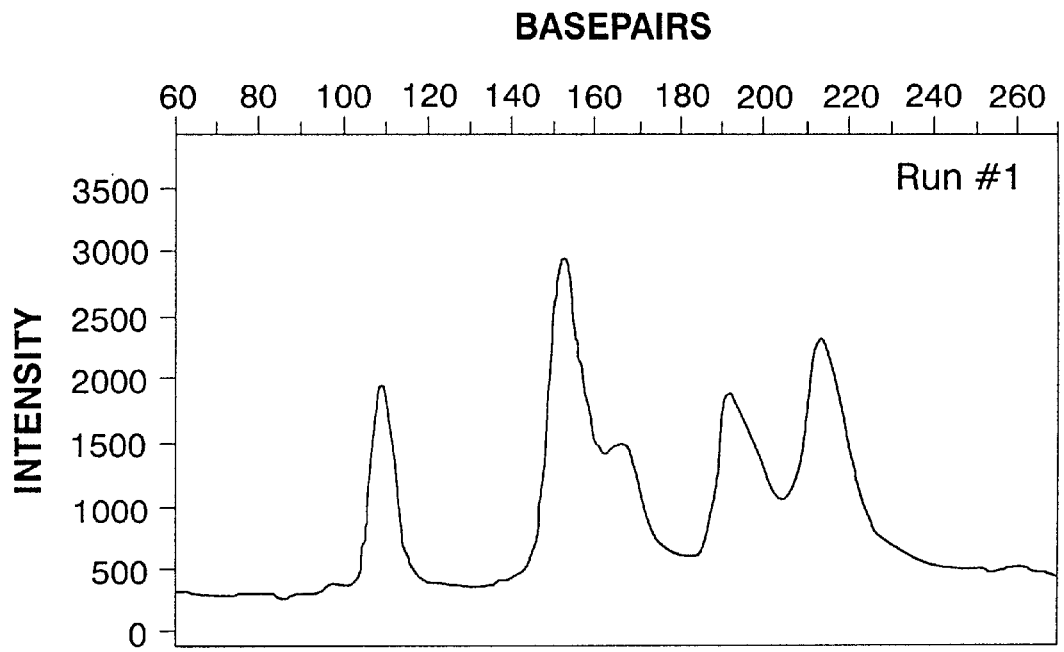
FIG. 6 shows the results of typing the same cell (R85-1518) on three separate occasions are shown. The intensity shown on the Y axis relates to DNA concentration and the sizes in basepairs are shown on the X axis. The profile of run 1 contains five major fragments at approximately 106, 152, 166, 193 and 214 bp. The profiles remain similar, although not identical as shown when superimposed in the lower panel. The panels show some of the effects expected from variations in total DNA concentration. There are also minor differences in fragment positions which are attributable to small variations which occur between separate electrophoresis runs.
Figure 6B:
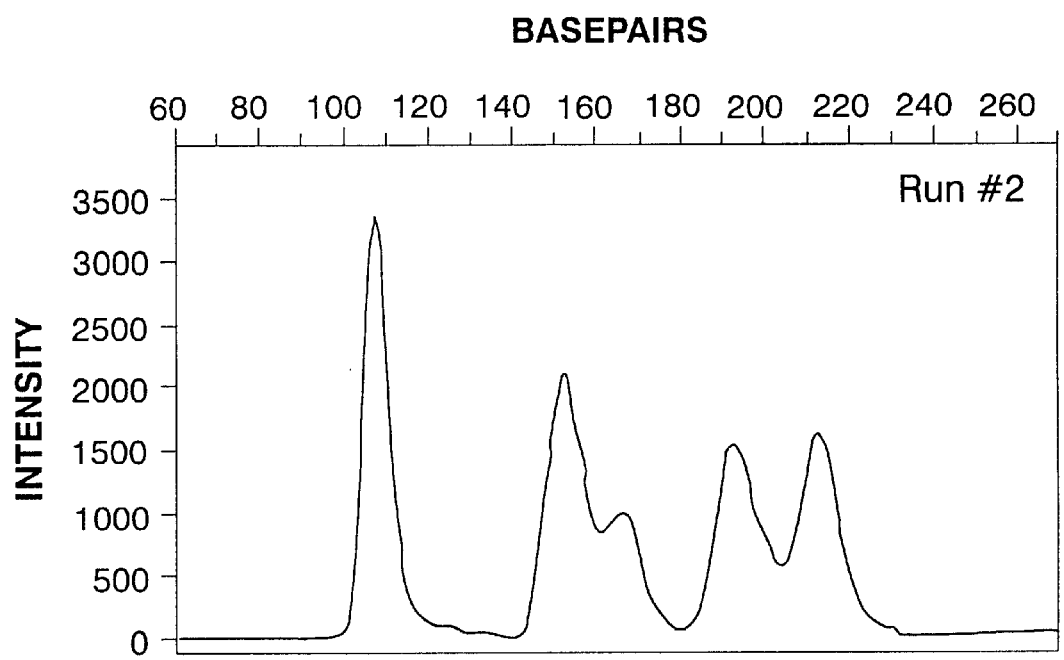
Figure 6C:
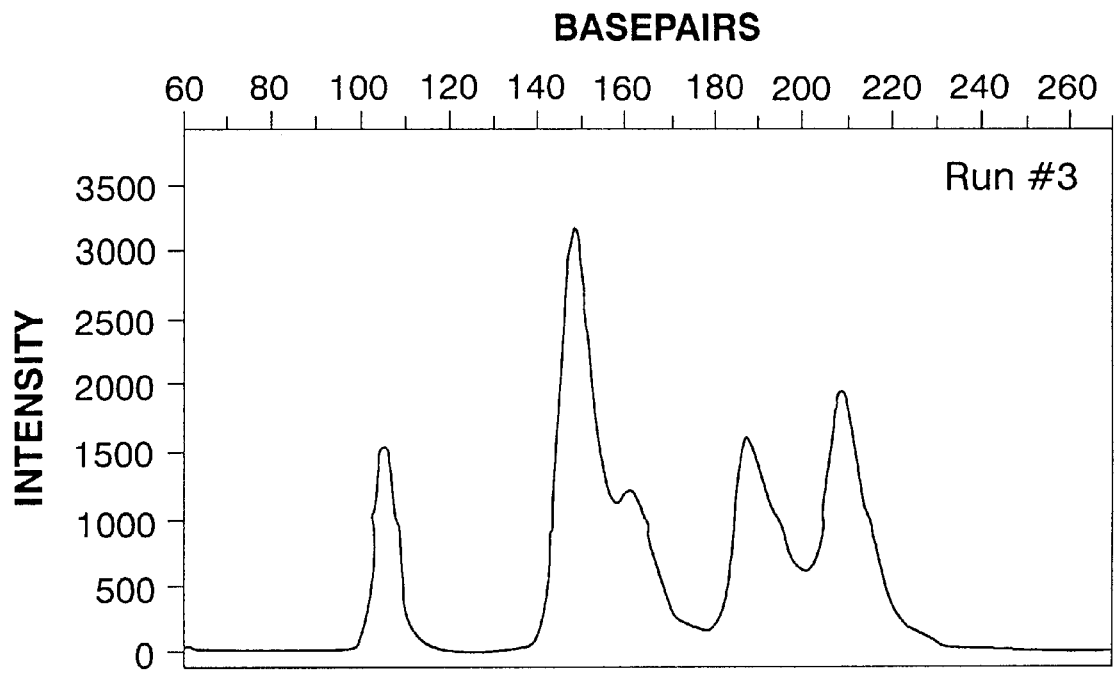
Figure 6D:
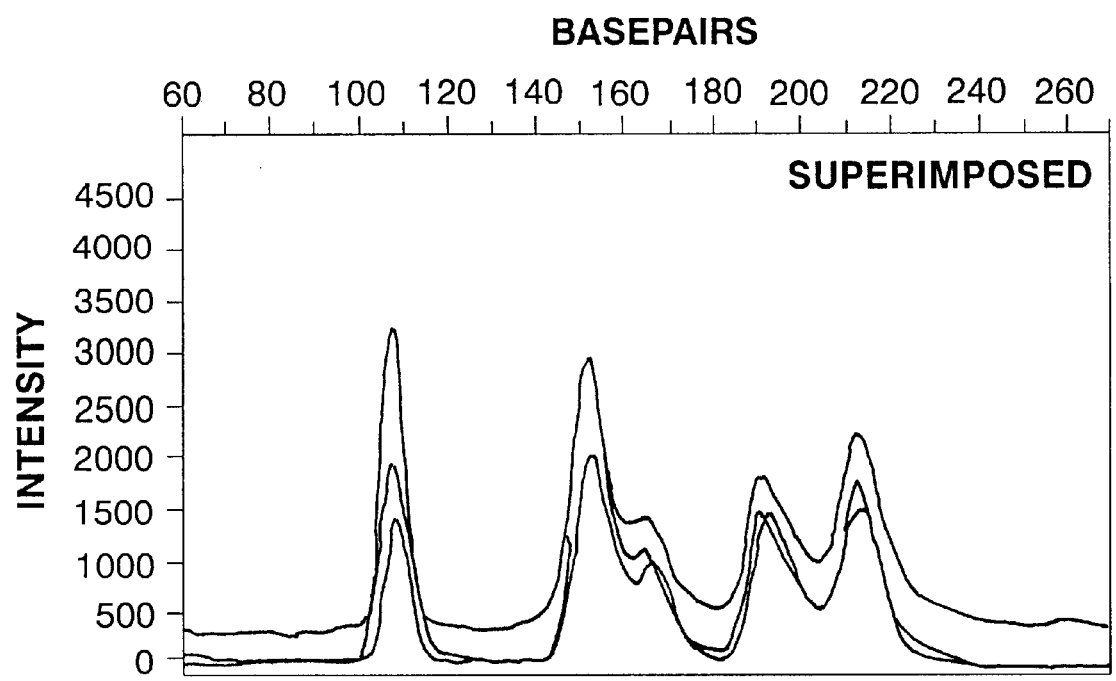

The resulting blot is shown in FIG. 5 (digestion with Taq I and Rsa I), and clear polymorphism is evident between ancestral haplotypes. Some of the patterns seen are specific for a particular ancestral haplotype. For instance, pattern F is carried only by the 65.1 ancestral haplotype.

EXAMPLE 4

Haplospecific Typing Patterns for the Beta Block and Delta Block of the MHC

There appear to be at least four distinct block of polymorphism within the MHC interval (FIG. 11). One block carries the HLA-A gene cluster (alpha block). The second block carries HLA-C, HLA-B, EC-1 and CL (beta block). A third block contains C4, C2, Bf and Cyp21 (gamma block) and the fourth block (delta) carries the DR and DQ gene clusters. Thus, the inventors believe that it will be sufficient to type for each of these polymorphic frozen blocks in order to identify ancestral haplotypes and their recombinants. It will also be possible to infer where recombination between ancestral haplotypes has occurred. Then it will be possible to map functions and diseases to particular polymorphic frozen blocks and to develop more clinical utility, for example, in relation to transplantation.

In this example, the inventors show that it is possible to recognise haplospecific typing patterns for the beta block and also the delta blocks.

Reproducibility for Each Cell

In the first instance, the variation seen when the same cell was typed on three different occasions, ie between runs was determined. As shown in FIG. 6, the number of fragments, the size of the fragments and the composite profiles were essentially identical on each occasion. Apparent variations are minor and can be attributable to differences in DNA concentration and to a lesser extent, electrophoresis conditions.

Reproducibility Between Genotypically Identical Siblings

Typing of nuclear families should allow an estimate of the value of the procedure as well as providing a means to determine whether the profiles are entirely accountable by sequences within the MHC. As shown in FIG. 7, siblings who inherited the same maternal and paternal ancestral haplotypes have very similar profiles with the same number of fragments present. Again the differences are minor and explicable in terms of DNA concentration.

Comparison of genotypically different siblings and comparison of siblings and parents should allow identification of the influence of both ancestral haplotypes carried by each subject. As shown in FIG. 7, ancestral haplotypes b and c must differ substantially, since ab and ac are quite different. Similarly, ac is quite different from cd, indicating that a and d generate different profiles. Until very large nuclear families have been types, it will not be possible to identify the precise contribution of each nuclear ancestral haplotype to the composite profile.

Matching for Identity

Given that the inventors demonstrated that patterns of genotypically identical siblings are at least very similar and that the patterns are complex as expected in heterozygotes, CL patterns in bone marrow donor/recipient pairs were then compared (FIG. 8). In three MHC genotypically identical sibling pairs the CL profiles of each recipient matched precisely the profile of the donor; ancestral haplotype sequences were identical by immediate descent. As expected the bone marrow grafts have done well. In five other pairs the donor and recipient were matched at HLA-A, B, C, DR and DQ but because haploidentity could not be inferred from family studies it was uncertain whether matching was complete. Unrelated pairs may appear to be matched in terms of HLA alleles but may be discordant to ancestral haplotypes and therefore genomic sequence.

Since some HLA alleles are carried by more than one ancestral haplotype and since HLA typing does not identify recombinant ancestral haplotypes, unrelated pairs may appear to be matched by HLA typing but may actually be discordant at the sequence level. In fact all five pairs were perfectly matched in terms HLA-A and B by serology and of PCR-SSO typing of DRB but CL typing revealed that two of the five differ at the beta block. The remaining three were precisely matched, as if related, suggesting sequence identity by remote descent from common ancestors. The two unmatched recipients lost their bone marrow grafts within 14 days whereas the other three have done well with successful engraftment and excellent functions for follow-up periods of 3 weeks to more than 1 year. Taking all 8 pairs there is a perfect correlation between CL matching and outcome (p<0.004 by Fischer's Exact Test). Thus, the present procedure provides an approach to matching which appears superior to conventional HLA typing.

Relationship to Ancestral Haplotype

The inventors explored the possibility that the patterns might be interpreted in relation to ancestral haplotypes. The aim was to define the twenty or perhaps fifty patterns which occur within a racial group at the beta block. In this way, it is possible to analyse results in relation to ancestral families, rather than small nuclear families with insufficient numbers available. As shown in FIG. 9, four unrelated subjects known to be homozygous for the 8.1 ancestral haplotype were compared. Thus, in effect, eight different ancestral haplotypes are being compared with the expectation of identity (shown in FIG. 9). In each individual the number of peaks is the same and the profiles are very similar with differences largely or wholly accountable by differences in DNA concentration. Thus, both nuclear and ancestral haplotypes give specific patterns and ancestral haplotypes should provide a useful basis for typing random heterozygotes.

Differences Between Different Ancestral Haplotypes

The present strategy is based on the assumption that there will be reproducible differences between all ancestral haplotypes. Some examples are shown in FIG. 10. It can be seen that seven different ancestral haplotypes give different patterns. Although in all cases homozygous cell lines are used and complexity is therefore reduced relative to heterozygotes, the differences appear to be sufficient to allow distinctions between all seven. In fact, as shown in Table 4, many more ancestral haplotypes have been compared and the differences found with only two exceptions. In both cases (46.1 versus 46.2 and 7.1 versus 7.2) the HLA alleles are shared. In these two cases, the specific sequences marked by the B allele have been retained since the separation of Caucasoids and Japanese (7.1 versus 7.2) and Chinese and Japanese (46.1 versus 46.2). However, in both cases the DRB patterns are different as expected (FIG. 11).

In contrast, on other ancestral haplotypes that appear to carry the same HLA-B allele (18.1 and 18.2), the B allele can be "split" serologically and by isoelectric focussing (IEF) and each has a distinct CL pattern and ipso facto unique beta blocks.

Haplospecific Typing Patterns for the Beta Block and Delta Blocks of the MHC

There appear to be at least four distinct blocks of polymorphism within the MHC interval (see also FIG. 11). One block carries the HLA-A gene cluster (alpha block). The second block carries (HLA-C, HLA-B, EC-1 and CL (beta block). A third block contains C4, C2, Bf and Cyp21 (gamma block) and the fourth block (delta) carries the DR and DQ gene clusters. Thus the inventors believe that it will be sufficient to type for each of these polymorphic frozen blocks in order to identify ancestral haplotypes and their recombinants. It will also be possible to infer where recombination between ancestral haplotypes has occurred. Then it will be possible to map functions and diseases to particular polymorphic frozen blocks and to develop more clinical utility, for example, in relation to transplantation. In this example, the inventors saw that it is possible to recognise haplospecific typing patterns for the beta block and also the delta blocks.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of said steps or features.

REFERENCES:

Banerji [1990], *Proc. Natl. Acad. Sci. USA* 87: 2374
Christian et al. [1991] *Bone Marrow Transplant* 8: 83–86
Compton [1991], *Nature* 350: 91–92
Dawkins et al. [1983], *Immunol. Rev.* 70: 5
French & Dawkiris [1990], *Immunology Today* 11: 271–274
Reed & Mann. [1985], *Nucleic Acid Res* 11: 7207
Sambrook, Fritsch & Maniatis [1989], *Molecular Cloning*; Cold Spring Harbor Laboratory Press, Cold Spring Harbor, N.Y.
Sargent et al. [1989], *Embo. J.* 8: 3205
Spies et al. [1989], *Science* 243: 214
Terasaki et al. [19761], *Manual of Tissue Typing Techniques, NIH Publication* 76: 546
Zhang et al. [1990], *J. Exp. Med.* 171: 2101

TABLE 4

Size and peak heights of fragments from 'CL' typing of different ancestral haplotypes

```
                       Size in basepairs
         1       1       1       2       2
         1       4       7       0       2
AH       0       0       0       0       0
44.2    20                              30   35       27
44.3     8                              23       14
13.1     3                              20            8
42.1     6    45                             14           9
57.1    37     2                55       17
44.1     1    48                             14           9
47.1    17    10                    16       23      19
18.2     3    70    71
 8.1    17     1            18        9      15       13
65.1     4    42                17        13
60.1     7    43                             14           9
 7.1     8    53                             16       12
 7.2     5    33                             11        8
62.1     2    63                             21           16
18.1     6    49                             15              11
46.1     1         40                        19       13
46.2     1         48                        18       14
60.3     6              51                   15              13
52.1     1              29                   14            9
58.1    14                  36        28
54.1     6                        26         16       17
55.1    19                        27     7   21       27
```

What is claimed is:

1. A method for determining whether the genome of an individual of a higher organism has the same ancestral haplotype as the genome of another individual of said higher organism, which comprises comparing haplospecific geometric elements (HGEs) within a multigene cluster of each individual, wherein said multigene cluster is the major histocompatibility complex (MHC), said HOEs consist of haplospecific sequences which are specific for a particular ancestral haplotype, and wherein the sequences flanking said HGEs are substantially conserved between ancestral haplotypes.

2. A method according to claim 1, wherein said comparison is based on at least one of:

(a) differences in the sequence of said HGEs;
    (b) differences in the length of said HGEs; or
    (c) differences in the number of HGEs.

3. A method according to claim 1, wherein said HGEs are compared by a method selected from the group consisting of DNA sequencing analysis, restriction fragment length polymorphism analysis, reaction with a haplospecific probe, heteroduplex analysis and primer directed amplification.

4. A method according to claim 3, wherein said comparison is based on at least one of:

(a) differences in the sequence of said HGEs;

(b) differences in the length of said HGEs;

(c) differences in the number of said HGEs; or (d) differences in the pattern of amplification products of said HGEs.

5. A method according to claim 3, wherein said method uses at least one oligonucleotide sequence of SEQ ID NO:16 or SEQ ID NO:17.

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 104 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

TCAGATCTCT CTCTCTCTCT CTCTCTCTCT GTGTGTGTGT GTCTCTCTCT C TCTCTCTCT          60

CTCTCTCTCT GTGTGTCTCT CTCTCTCTCT CTCTCTCTCT GTTT                          104

(2) INFORMATION FOR SEQ ID NO:2:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:2:

TCTCTCTCTC TCTCTCTCTC TCTCTCTC                                             28

(2) INFORMATION FOR SEQ ID NO:3:

(i) SEQUENCE CHARACTERISTICS:
             (A) LENGTH: 56 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:3:

TCTCTCTCTC TCTCTCTCTC TCTCTCTCTC TCTCTCTCTC TCTCTCTCTC T CTCTC             56

(2) INFORMATION FOR SEQ ID NO:4:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:4:

TCTCTCTCTC TCTCTCTCTC TCTCTCTCTC                                           30

(2) INFORMATION FOR SEQ ID NO:5:

(i) SEQUENCE CHARACTERISTICS:
             (A) LENGTH: 58 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:5:

TATCTCTCTC TCTCTCTCTC TCTCTCTCTC TCTCTCTCTT TCTCTCTCTC T CTCTCTC           58

(2) INFORMATION FOR SEQ ID NO:6:

(i) SEQUENCE CHARACTERISTICS:
             (A) LENGTH: 96 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:6:

```
TCTCTCTCTC TCTCTCTCTC TCTCTCTCTC TGTCTCTCTC TCTCTCTCTG T CTCTCTCTC      60

TCTCTCTGTC TCTCTCTCTC TCTCTGTCTC TCTCTC                                 96
```

(2) INFORMATION FOR SEQ ID NO:7:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
TCTCTCTCTC TCTCTCTCTC TCTCTCTCTC TGTCTCTCTC TCTCTCTCTG T CTCTCTCTC      60

TCTCTCTGTC TCTCTCTCTC TCTCTGTCTC TCTCTC                                 96
```

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
ACAAGCCCCC AGCAGAATTC TGCTTTTCAA A                                      31
```

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
CAAGTCTCAA TATTCAGTAG CTGTGACTTC TGGATAGTC                              39
```

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
CAAGTCTCAA TATTGAGTAG CTGTGACTTC TGGATAGTC                              39
```

(2) INFORMATION FOR SEQ ID NO:11:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CAAGTCTCAA TACTGAGTAG CTGTGACTTC TGGATAGTC                              39

(2) INFORMATION FOR SEQ ID NO:12:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

TGTAAAACGA CGGCCAGTAC AAGCCCCCAG CAGAATTCTG CTT                         43

(2) INFORMATION FOR SEQ ID NO:13:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

CAGGAAACAG CTATGACCGA CTATCCAGAA GTCACAGCTA CTC                         43

(2) INFORMATION FOR SEQ ID NO:14:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

TGTAAAACGA CGGCCAGTAC AAGCCCCCAG CAGAATTCTG CTT                         43

(2) INFORMATION FOR SEQ ID NO:15:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

CAGGAAACAG CTATGACCGA CTATCCAGAA GTCACAGCTA CTC                         43

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

ACAAGCCCCC AGCAGAATTC TGCTT                                             25

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

```
GACTATCCAG AAGTCACAGC TACTC                                          25
```

(2) INFORMATION FOR SEQ ID NO:18:

(i) SEQUENCE CHARACTERISTICS:
        (A) LENGTH: 6405 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

```
CCTTCATATT TTCATGTCAT TGAATCTTTC TTAAAGTGCC TTTGAAAGAG A TGTTTTCAG      60
TGGAATAGAG AGATGTGTAA CAATATTTAC AAAAGGGGTT GGCTGTAATA A AAAGGGAAA    120
CGCAAATGAG TGGGGACACA GGGGACCCTG TTCCATTTAT TCTCAAAGCA C GTTTGAAAA    180
CTGCGTTGCC ATAGCGTCCT TGGATGGAGA CAAAGTCGAG GCAGATCTTG T TCCTGGAGT    240
ATTGATTTGA TTTTGGAAAC GGTCCAAGGC TTTCAGGAAT CAGGCTGACT T AGATCTAAA    300
GTCTCAAGAA TGTTCGTTCT AGCAGTGAGC CTGTGAGAAG AATCTAGCCC A TCTGGGCGA    360
TGCTCTCTCT GCTTTCACCT AGTGGCAGTG GTTGGAAGGA CAGGGCACAG T GTTACTGCA    420
TGGGTGGGGC TGAAGCCAAG GTGAAACCGC CTTTGGSAAA TTATAAGTAA G GAAATGATG    480
ACAGTGAAAG ACATCAAACC TAACTCACCC TATCTTGCTT CTAACCGCTA A CCTGCCCTT    540
GTTCATTTCT GGGCATAGGC CGAACTAGCC TTGGGAAGGA ATTTATAGTT T AAAGGGAAA    600
GTGTTCTTTT AAAACGAATG AAAGGCCGCC AGCCATTAAG TTAGGATGAG A GGGGCTGGA    660
ATTCTGAATA TTACCAGCCA TTATTCCGGA GGTCATAAGA TTTGCAACTT C CCCAGTTAC    720
TCTTGAAGGT AACATCACTA TTGTGAACCT CAGAGCGGCC TTTTGAGATG T ATTTTTCAT    780
TTCTTTTTTC TTTTTCTTTC TTTCTTTTCT TTTCTTTTTT TTTTTTTTTT T TTTGACGGA    840
GTCTCGCTCT GTCGCCCAGG CTGGAGTGCA GTGGCGCGAT CTCGGCTCAC T GCAAGCTCC    900
GCCTCCCGGG TTCACGTCAT TCTCCTTCCT CAGCCTACTG AGTAGCTGGG C CCGCCACCA    960
CCCGCCACCA CACCCGGCTA ATTTTTTGTA TTTTTAGTAG AGACGGGGTT T CACCGTGTT   1020
AGCAAGGATG GTCTCCATCT CCTGACCTCG TGATCCGCCC GCCTCGGGCT C CCAAAGTGC   1080
TGGGATTACA GGCGTGAGCA CCACGCCAGG CCAGGTTTTT GCATTTCTAA C AACTGGAGG   1140
ACCCCATCTG GACCTGCCAA CCAGTCCTGT GGCCCCCCAC TCAGGAACTG A CTCAGCCTA   1200
AGAGAACAGC TCCACTCACT ATGATTTCAT ACCGGGCCA ACCAATCAGC A CTCCTGATT   1260
CACTGGCCCC CCCTATCCAC CAAATTATCC TTAAAAACTG ATCAGAGTTT T CGGGGAGAC   1320
AGATTTGAGT AATAAAACTC TGGTCTCCCG CACGGCCGGC TCTGCATGAA T TACTCTTTC   1380
TCTATTGTAA TTCCCCTGCC TTGATAAATC GGCTTTGTCT AGGCAGTCAG C AAGGTGAAC   1440
ACACTGGGTG GTTACAAAGG GAGTCCAGGC CAGTGTGCAG GATGTGCTTT G CTGTAGTGG   1500
```

-continued

```
GGTCCGGGTA GCGGAGGAAA GTCAAGGACA CTCAGGGAAT AAATGGCAGA G GAAGAAGGA    1560

GCACGAGGGA GGACCCAAAG CCTCCAGACC TCTCCTTCCT TCTCTCCCTG T TAGGGTTGG    1620

AGAGGACCAG CGTGGTCCCA GGAGGGATGG CTGGTGGGGT GCAGAAAACG C CCTGGTTGC    1680

AAAGGGGCGT CACGCGCCCC ACACAAGGGT CCTGGCTGTC AGCTGCTACT C ATGAGTTCA    1740

AATTAGGAGG AGACTCACAC GTGTCCTTTG CAAGGTAGAC TCCTTATCTC C CGCTCCGGC    1800

TGGGTTCCCA AATCCATCCT GATAAAGCAC AAAAACCAAG AGCCAAATTC T GCGTGGGAC    1860

CTTTCTGACA GCTGGAAGGT CCTCCCCCTC CCCATTCCTC ACATGTGCCC T TCTTGCCCT    1920

GCCCCCTCCA CTTTGTCTCC ACTTCCTCAT CCTTTTCCCT CTCCGGACCC G CTCCTGAGT    1980

ATCTCCCGCC TTCTTCAGAG GACTTCTCCT CATGAAGTAC AGACTCCTCC A CCTCCAGGA    2040

AAAAGAGACA AAGACCACTG AGAGGACCT GAGAAATGCC TGTGACCCAC C CCTGAGGGC    2100

AGCCYCTCCC TCAGTGCTGG CTCTGGCTGT GTGTGTGTAT GTATTTTGTT T TGTTTTGTT    2160

TGTTTGTTTT TGAGACAGGG TCTCACTCTG ATGGTCAAGC TAGAGCAGTG T CCTGATCAC    2220

AGCTCATTGC AGGCTCCAAC TCCTGGATTC AGGCAATCCT CCTACCTCAG C TTCTTGAGT    2280

AGCTGGGACT ACAGACTGGA GCCACCACAC CCAGTATGTG TGTGTGTGTG T GTGTGTGTG    2340

TGTGTGTGTG TATTTTTTTC TTTTCTTTTC TTTTTTTTTT TTTTGTAGAG A CTGGGTCTT    2400

GCTTTGTTAC CCATGCTGGT CTTGAACTTC TGGCTTCAAG CAATTCTCAT G CCTCAGCCT    2460

CCCAAAGTGC TGAGATTACG GGCATAAACC ACAACGCCTG GCCCCTGTGT G TGTACATAC    2520

AAAGTCAAAG TGCTAAACCT GGCACCTAGG AAACATCCCC ACCTTGGCAT T GCTTGCAAC    2580

AGTCGGTATT TTGTGCACCT GTGCTTTTGT TTCGGGAGCT GGGACAATTA T ATTCATCAG    2640

AACAGCACGG TGTTAAGGCC CTCACCCCCA GAAAGCTTAA GGGACACTGT T TTATGAAGG    2700

AGAGTGAGAT TGGAGGAGCC CCTGACTCCA GGTCTCCTGA TCCTTCTTAC A CAAAGCGAT    2760

GCTGAAAAAA AGTGCAGGAC ACTCCATTTC CTCCTGGGAC CAGACAGGGA A GCCAGAGCC    2820

ACTGTGGATG TCAAATTCCA CCAAGGAAAT ACCAGTATAG AAAATCTCCA C GTCACATTT    2880

TAAAGCTCAC ACAAGGGCTC AAAGAGAACC CACGTCAAAA AACCGAATTC C TAGCTCAGG    2940

TGAGATCACC AAATTTGCCT GTGAGGTTTT GTGGAACCTG CAGGTAGAAA G GACATCTTT    3000

ATTTAGAGCT GCAGCCCAAT TGCTCCTGCA TCTTGGGGCC CCTTGAAAGG A CCCTCTCCC    3060

TTCAACAGTG CATAGTGAGG CCATTTCTGG GGAGAAACGT AGACTGTCCT T GGACTCCTG    3120

AGGTTTTTAC ACTTACTTGC TGACTCTGTG GACTTTGACT TCATCATTAA A CATCTTACA    3180

ACGATGTAAT TTGCTTTGAC TGTAAGTATA GAACAGGACA CTGTTCCTGA A GCAGGAAAC    3240

AAGGGACTGG TGACCTGAAC TGCCACCCCC CTCCCTGGTG CTCAGATGTA A TGAAATCGT    3300

GAGGCAACAA ATCTATGGCT AGGTAAAGGG TCAACTCCAT TTCAGCAAAT G TTTCAGATG    3360

TTCCTTCCCG CCTAGTAATG TTCCAGCTTT ACCCCAGCCT TAATCTTTTA A AATGTATAT    3420

TTTCCTTGGT GTTATTTTAA AGTAATTCGT ATGTATTTAT TACACTGGGT T TGTTGCAGT    3480

AAGCCACTTC GAATGTTGCT GTAGAATTAA AGTAAGCAAA TAAATGTGTG G TTCTCCACG    3540

GAGTTACTAA CTCTTAAAAA AAAAAGTCCA AATGTCCATT CCCAACTCAG C TTCAAGGAA    3600

AGTCTCCTCT AGACTCCACA GGGTAGAAAT TCCTGTTGAT GGCACCTTCA G AAGGTAAGA    3660

AAGGAACTCT TCCTCCACCA TGCCTGACCC ATCTTTGGGT TTAGGCATT G GCCGACTGA    3720

TAAAGGCAAC TCTGAGAGTA CAATCCATGT ATAGATGACC GATAGTCATA T AATAGGAAT    3780

CTCACCACAC CTGAGAGAGT GGGATAGATT CTCTCATTTT CATAGTTTGG G CATCTGAGT    3840

CTCTGAGAGC CTGAATGCCT GACATGGATT CTCCAAGAAT GTTGGCCTTG A GACTCTAAA    3900
```

```
GGGCCCCGGG TCTCCTGTGA AGCCCCCTGT GCATGCACCA CACCCGCAGA G GCTCCACAA   3960

CGGCGGGAAG AGCACCCAGG GTCAGAGCCC AGGCGAGTTC ACACTCGGGG A CCATCCACA   4020

TCCAGGGCGT GCAGGGGAGG GGCCGAGGTG AGAGCCCAAC CCCTGCCTAG G CTGTGGTGA   4080

CTGGTGGCTG CACGGGGGTC CCAGCGCTCC TGGAGCTATC ATTCTTTATC T CCTGAAGAC   4140

CCCGGACCCG CACATACAAA ACTCTGCATT TCTGGTGGAG CGGTCTTCTC T TTTGAGATG   4200

TAAACACTAC TTCTCGAATC TTAAAGCCAG CCATTGCCAC TCCTAAGGGA T AAGCCTCTA   4260

ACTCCACTGA AATTAGCCTC AGAATTTCAG CTGAGCATTT GGAGCCACAG G CAGGAAGTC   4320

TGTGGGATTT GTACCTGGCT GATCTGGAAG GTGGTCCTGA AAGGTAGTGT G TGACTAGGT   4380

GGGCTTTGAG GGGCATGGAA GTCCCTGATG AGAGGAGAAC AAGACAGATG G GAAGGTTCC   4440

GAAAGTGAAT TTCAGTGGGC CCTGTGCCCA GCACTAGGAT TTGGAAAATC T TTTCCCAGC   4500

CACTTTTGGC CTGTGGGTTT TCATTCTGCT TTCCTGTCTG CCAAGCCATT C CAGGCAATC   4560

CCTTCATTTG GTAAACATTT ATCAAATACC TACTGTGCGT GGGGCATTGT T TTAAGAGGA   4620

GCTGGAACTG AGGTAAGAGG AAATAAACCC TCCTTGCCCT CAAGGCGTGC C CAGTCTTGC   4680

TCAGGCAGAG ATCAGTAAGG AAATCATAAC ACAAATTGAG AGAGAAAAAA A GGAAGAAAC   4740

TGGTCAGGCG GCAGTTATG GTGGGTTCTC AGTTGAATTA TTTCAAACAA A AGAACGTCC    4800

TGCAGGCACA GAGAAGGGAA CTTGCACAGG GGGCTTGCC TAAGACATGC C CACAGCTGC    4860

ACAAATAAGA AAGGCTGCAC AGGAGACTTG TCCAGACATG CCCGCAATGG A AAATTCTGT   4920

CCCCCGATAC ATGGGCAGTC AGGGAAACAA GCCAATATGG AGTAACTCAA G CTAAGGGCC   4980

TGCATGGGCA CTAGGAGGAT GGGGTGGAGC TACCGGAAAT TCGTGCCTTA T GCAAATGAG   5040

ACACCCAGCC CTCATCAGTT TCTTGTAAAA GCCTTTGCAT TCAGCTGTAA A AATGGCAAC   5100

CATCTTCCAA GCCCCCTCTC TGCAGGGGAG AGCTTTCTTC TTTTGCTTAT T AAACTTTTG   5160

CTCCAACCTC ACCCTTTGTA TCCACGCTCC TTAATTCTCT TGGTGGTGAG A CAAATAACT   5220

CCAGGTAACA CCTCACAAGG AGAGACTGAG AGGCTGCTAC GTTGTGGTGC A TTGGCAAGA   5280

CTAACAAACT GGCTAGTGGG ACATGCACAC TTGCTTGGTA GACATATATG T AGATCTTCA   5340

GCTCTGACTA ATGAAGGAAT ACCAAAAATC TCATAAAAGA AAAAAATATT A TTTGAGCTT   5400

TGTTTTGTGG TGTAAGTGGG AGCCCCACAG GCACCCAGGA TAGGAGAGCT T TGCTCAGAA   5460

TCCAGGAAGT GAACATCTTT CCCTGGGCCA GGCAAGAAT GAGACTAAGC T GATTGAGGA    5520

GCCTGGTGCC TCCTGGCAAG AAAGGGTGTC TGACACCTGA CTATCCAGAA G TCACAGCTA   5580

CTGAATATTG AGACTTGAAA CAGAGAGAGA GAGAGAGAGA GAGAGACACA C AGAGAGAGA   5640

GAGAGAGAGA GAGAGAGAGA CACACACACA CAGAGAGAGA GAGAGAGAGA G AGAGATCTG   5700

ATTTGAAAAG CAGAATTCTG CTGGGGGCTT GTTAAATGCA GAGTTTCTGA T ACAGTAGGT   5760

CCAGGCCAGG CCCTGAAGAT TGCATATCTA AGTTCCCAGG TGATGCCAAT G CTGCTTCCC   5820

CCAGGACCAC ACTTTGAGAA CCACCACCCT AAGGCAATCT GTGTTGGTTT C TAATATCAG   5880

AAGAGGGCTG GGAGTGGGCT GGGAGGCAGA GGTGTAGGAT CAGTGAGACC A CACCTGACC   5940

CACCCTGGAC AGCTCCCCAC CCCAATCTTG CAGCATTTTA TTTCCTGGGA G TCCTGGGAA   6000

TGGAAGACAC CCAGGAAGGG ACCAAATGTG GGGTCACAGG GTGATCCAGA G GCTCGGCTT   6060

CATACAGCAC CTGGGGCTCC CGCCACTCCA CAACTGGCCC CCACACCCTC A GTCTTCCCA   6120

CCCCTCACGA CACTGACCTC CAGACCTTCC TCGACTGCTC TCAGCAGGTT G GGCCTGGGA   6180

TGTGACACTA GGAGCTCTGA GTGTACCTTC TGATCCAAAG ATAGGGTGAC T GCGTATGAC   6240
```

```
AAGTACTCAG ATGGGCCATT AATAAGACCT TGAACATTTG GCAAATGGCT T CAGTCACGT      6300

GTGCTTGAGA ATTCCAGTGT TTTCTAGATA TGGCATCCAT GAGCCCACAC A AACACTGGA     6360

GGGCGTCGTG AGCATACTGA AACCCATAAC TGCTGCACTG GATCC                      6405
```

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

```
TGGAACAGCC AGAAGGAC                                                      18
```

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

```
GATAGAGAGG ATTCTAAATG                                                    20
```

(2) INFORMATION FOR SEQ ID NO:21:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

```
TGTGTGTGTG TG                                                            12
```

(2) INFORMATION FOR SEQ ID NO:22:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

```
TGTGTG                                                                    6
```